(12) United States Patent
Overstreet et al.

(10) Patent No.: US 8,190,271 B2
(45) Date of Patent: May 29, 2012

(54) MINIMIZING TRAUMA DURING AND AFTER INSERTION OF A COCHLEAR LEAD

(75) Inventors: Edward H. Overstreet, Valencia, CA (US); Michael A. Faltys, Valencia, CA (US); Jian Xie, Stevenson Ranch, CA (US); Michael S. Colvin, Thousand Oaks, CA (US)

(73) Assignee: Advanced Bionics, LLC, Valencia, CA (US)

( * ) Notice: Subject to any disclaimer, the term of this patent is extended or adjusted under 35 U.S.C. 154(b) by 804 days.

(21) Appl. No.: 12/202,134

(22) Filed: Aug. 29, 2008

(65) Prior Publication Data
US 2009/0062896 A1 Mar. 5, 2009

Related U.S. Application Data

(60) Provisional application No. 60/968,785, filed on Aug. 29, 2007.

(51) Int. Cl.
*A61N 1/05* (2006.01)
(52) U.S. Cl. ........................ 607/137; 607/116
(58) Field of Classification Search .................. 607/116, 607/119, 120, 137
See application file for complete search history.

(56) References Cited

U.S. PATENT DOCUMENTS

| | | | |
|---|---|---|---|
| 3,416,531 A | 12/1968 | Edwards | |
| 3,572,344 A | 3/1971 | Bolduc | |
| 3,751,605 A | 8/1973 | Michelson | |
| 3,924,632 A | 12/1975 | Cook | |
| 4,033,355 A | 7/1977 | Amundson | |
| 4,355,646 A | 10/1982 | Kallok et al. | |
| 4,400,590 A | 8/1983 | Michelson | |
| 4,432,377 A | 2/1984 | Dickhudt | |
| 4,458,695 A | 7/1984 | Peers-Trevarton | |
| 4,506,680 A | 3/1985 | Stokes | |
| 4,559,951 A | 12/1985 | Dahl et al. | |
| 4,608,986 A | 9/1986 | Beranek et al. | |
| 4,640,983 A | 2/1987 | Comte | |
| 4,711,251 A | 12/1987 | Stokes | |
| 4,819,647 A | 4/1989 | Byers et al. | |

(Continued)

FOREIGN PATENT DOCUMENTS
EP 0747069 B1 9/2002
(Continued)

OTHER PUBLICATIONS

RC Beck et al, "Nanoparticles containing dexamethasone: Physicochemical properties and anti-inflammatory activity", Acta Farmaceutica Bonaerense (Argentina), vol. 22, No. 1; Nov. 15, 2003.

(Continued)

*Primary Examiner* — George Evanisko
(74) *Attorney, Agent, or Firm* — Steven L. Nichols; Van Cott, Bagley, Cornwall & McCarthy P.C.

(57) ABSTRACT

A method for delivering dexamethasone base (DXMb) via an implantable electrode includes coupling DXMb to the implantable electrode and inserting the implantable electrode into animal tissue, the DXMb eluting into the animal tissue. An implantable nerve stimulating device includes an elongated member having a distal end bearing at least one electrode; and DXMb coupled to the elongated member, the DXMb being eluted into tissue surrounding the elongated member.

6 Claims, 13 Drawing Sheets

U.S. PATENT DOCUMENTS

| | | |
|---|---|---|
| 4,840,186 A | 6/1989 | Lekholm et al. |
| 4,899,787 A | 2/1990 | Ouchi et al. |
| 4,944,088 A | 7/1990 | Doan et al. |
| 4,991,152 A | 2/1991 | Letiche |
| 5,037,404 A | 8/1991 | Gold et al. |
| 5,057,092 A | 10/1991 | Webster, Jr. |
| 5,092,332 A | 3/1992 | Lee et al. |
| 5,095,905 A | 3/1992 | Klepinski |
| 5,103,837 A | 4/1992 | Weidlich et al. |
| 5,119,832 A | 6/1992 | Xavier |
| 5,383,922 A | 1/1995 | Zipes et al. |
| 5,411,545 A | 5/1995 | Breyen et al. |
| 5,423,881 A | 6/1995 | Breyen et al. |
| 5,443,493 A | 8/1995 | Byers et al. |
| 5,496,306 A | 3/1996 | Engelhardt et al. |
| 5,496,360 A | 3/1996 | Hoffmann et al. |
| 5,545,219 A | 8/1996 | Kuzma |
| 5,578,084 A | 11/1996 | Kuzma et al. |
| 5,580,699 A | 12/1996 | Layman et al. |
| 5,603,726 A | 2/1997 | Schulman et al. |
| 5,609,629 A | 3/1997 | Fearnot et al. |
| 5,626,629 A | 5/1997 | Faltys et al. |
| 5,630,839 A | 5/1997 | Corbett et al. |
| 5,645,585 A | 7/1997 | Kuzma |
| 5,653,742 A | 8/1997 | Parker et al. |
| 5,658,263 A | 8/1997 | Dang et al. |
| 5,658,709 A | 8/1997 | Layman et al. |
| 5,697,951 A | 12/1997 | Harpstead et al. |
| 5,728,063 A | 3/1998 | Preissman et al. |
| 5,788,979 A | 8/1998 | Alt et al. |
| 5,824,049 A | 10/1998 | Ragheb et al. |
| 5,833,714 A | 11/1998 | Loeb |
| 5,929,041 A | 7/1999 | Magal |
| 5,931,864 A | 8/1999 | Chastain et al. |
| 5,938,596 A | 8/1999 | Woloszko et al. |
| 5,938,691 A | 8/1999 | Schulman et al. |
| 5,957,970 A | 9/1999 | Shoberg et al. |
| 5,987,746 A | 11/1999 | Williams |
| 6,018,683 A | 1/2000 | Verness et al. |
| 6,026,567 A | 2/2000 | Swoyer et al. |
| 6,038,482 A | 3/2000 | Vachon |
| 6,038,484 A | 3/2000 | Kuzma |
| 6,052,625 A | 4/2000 | Marshall |
| 6,067,474 A | 5/2000 | Schulman et al. |
| 6,070,105 A | 5/2000 | Kuzma |
| 6,091,979 A | 7/2000 | Madsen |
| 6,112,124 A | 8/2000 | Loeb |
| 6,119,044 A | 9/2000 | Kuzma |
| 6,125,302 A | 9/2000 | Kuzma |
| 6,129,753 A | 10/2000 | Kuzma |
| 6,144,883 A | 11/2000 | Kuzma |
| 6,157,861 A | 12/2000 | Faltys et al. |
| 6,195,586 B1 | 2/2001 | Kuzma |
| 6,198,973 B1 | 3/2001 | Doan et al. |
| 6,208,881 B1 | 3/2001 | Champeau |
| 6,249,704 B1 | 6/2001 | Maltan et al. |
| 6,259,951 B1 | 7/2001 | Kuzma et al. |
| 6,289,247 B1 | 9/2001 | Faltys et al. |
| 6,304,787 B1 | 10/2001 | Kuzma et al. |
| 6,309,410 B1 | 10/2001 | Kuzma et al. |
| 6,343,226 B1 | 1/2002 | Sunde et al. |
| 6,379,353 B1 | 4/2002 | Nichols |
| 6,415,187 B1 | 7/2002 | Kuzma et al. |
| 6,501,991 B1 | 12/2002 | Honeck et al. |
| 6,522,932 B1 | 2/2003 | Kuzma et al. |
| 6,567,705 B1 | 5/2003 | Stokes et al. |
| 6,665,563 B2 | 12/2003 | Stokes et al. |
| 6,754,536 B2 | 6/2004 | Swoyer et al. |
| 6,801,805 B2 | 10/2004 | Stokes et al. |
| 6,862,805 B1 | 3/2005 | Kuzma et al. |
| 6,879,695 B2 | 4/2005 | Maltan et al. |
| 7,044,942 B2 | 5/2006 | Jolly et al. |
| 7,146,227 B2 | 12/2006 | Dadd et al. |
| 7,187,981 B2 | 3/2007 | Tanaka |
| 7,206,639 B2 | 4/2007 | Jacobsen et al. |
| 7,218,971 B2 | 5/2007 | Heil, Jr. et al. |
| 7,272,449 B2 | 9/2007 | Dadd et al. |
| 7,282,213 B2 | 10/2007 | Schroeder et al. |
| 7,294,345 B2 | 11/2007 | Haapakumpu et al. |
| 7,337,011 B2 | 2/2008 | Stokes et al. |
| 7,363,091 B1 | 4/2008 | Chen et al. |
| 7,406,352 B2 | 7/2008 | Gibson |
| 7,412,290 B2 | 8/2008 | Janke et al. |
| 7,445,628 B2 | 11/2008 | Ragheb et al. |
| 7,451,000 B2 | 11/2008 | Gibson et al. |
| 7,571,012 B2 | 8/2009 | Gibson |
| 7,815,615 B2 | 10/2010 | Jolly et al. |
| 7,867,193 B2 | 1/2011 | McKenna et al. |
| 7,867,194 B2 | 1/2011 | Fiering et al. |
| 2002/0077685 A1 | 6/2002 | Sundquist et al. |
| 2002/0138123 A1* | 9/2002 | Casas-Bejar et al. ......... 607/120 |
| 2004/0078057 A1 | 4/2004 | Gibson |
| 2004/0215306 A1 | 10/2004 | Heil et al. |
| 2004/0220510 A1* | 11/2004 | Koullick et al. .................. 604/8 |
| 2004/0236390 A1 | 11/2004 | Dadd et al. |
| 2005/0186244 A1 | 8/2005 | Hunter et al. |
| 2005/0256560 A1 | 11/2005 | Lenarz et al. |
| 2006/0004432 A1 | 1/2006 | Parker et al. |
| 2006/0039946 A1 | 2/2006 | Heruth et al. |
| 2006/0184143 A1 | 8/2006 | Jolly et al. |
| 2006/0247749 A1 | 11/2006 | Colvin |
| 2006/0264897 A1 | 11/2006 | Lobl et al. |
| 2006/0282123 A1 | 12/2006 | Hunter et al. |
| 2006/0287689 A1 | 12/2006 | Debruyne et al. |
| 2007/0026041 A1 | 2/2007 | Desnoyer et al. |
| 2007/0073130 A1 | 3/2007 | Finch et al. |
| 2007/0073371 A1 | 3/2007 | Dadd et al. |
| 2007/0088335 A1 | 4/2007 | Jolly |
| 2007/0179566 A1 | 8/2007 | Gantz et al. |
| 2007/0198063 A1 | 8/2007 | Hunter et al. |
| 2007/0203557 A1 | 8/2007 | Gantz et al. |
| 2007/0213799 A1 | 9/2007 | Jolly et al. |
| 2008/0014244 A1 | 1/2008 | Gale |
| 2008/0033520 A1 | 2/2008 | Jolly |
| 2008/0039771 A1 | 2/2008 | Jolly |
| 2008/0269864 A1 | 10/2008 | Dadd et al. |
| 2009/0012594 A1 | 1/2009 | Gibson |
| 2009/0043369 A1 | 2/2009 | Radeloff |
| 2009/0043370 A1 | 2/2009 | Gibson et al. |
| 2009/0048580 A1 | 2/2009 | Gibson |
| 2009/0062896 A1 | 3/2009 | Overstreet et al. |
| 2009/0076581 A1 | 3/2009 | Gibson |
| 2009/0259267 A1 | 10/2009 | Jolly |
| 2009/0292329 A1 | 11/2009 | Gibson |
| 2010/0030130 A1 | 2/2010 | Parker et al. |
| 2010/0106134 A1 | 4/2010 | Jolly et al. |
| 2010/0121256 A1 | 5/2010 | Jolly et al. |
| 2010/0121422 A1 | 5/2010 | Jolly et al. |
| 2010/0256697 A1 | 10/2010 | Carter et al. |
| 2011/0098813 A1 | 4/2011 | Gibson |
| 2011/0224629 A1 | 9/2011 | Jolly et al. |

FOREIGN PATENT DOCUMENTS

| | | |
|---|---|---|
| EP | 1340408 | 9/2003 |
| EP | 1024855 B1 | 11/2003 |
| EP | 1441679 | 8/2004 |
| EP | 0971660 B1 | 9/2004 |
| EP | 1604626 A2 | 12/2005 |
| EP | 1604626 A3 | 12/2005 |
| EP | 1340408 B1 | 10/2008 |
| EP | 1604626 B1 | 12/2008 |
| EP | 1425940 B1 | 3/2009 |
| EP | 2042137 A1 | 4/2009 |
| EP | 2047884 A1 | 4/2009 |
| EP | 2108399 A1 | 10/2009 |
| EP | 1478433 B1 | 11/2009 |
| WO | 9710784 | 3/1997 |
| WO | 9710784 A1 | 3/1997 |
| WO | 9922806 | 5/1999 |
| WO | 9922806 A1 | 5/1999 |
| WO | 0228473 | 4/2002 |
| WO | 0228473 A1 | 4/2002 |
| WO | 0228474 | 4/2002 |
| WO | 0228474 A1 | 4/2002 |
| WO | 0232498 A1 | 4/2002 |
| WO | 0241666 A1 | 5/2002 |
| WO | 0243623 A1 | 6/2002 |

| | | | |
|---|---|---|---|
| WO | 02071984 A1 | 9/2002 |
| WO | 03024153 A1 | 3/2003 |
| WO | 03034960 A1 | 5/2003 |
| WO | 03072193 A1 | 9/2003 |
| WO | 2004050056 A1 | 6/2004 |
| WO | 2006079055 A2 | 7/2006 |
| WO | 2006083675 A2 | 8/2006 |
| WO | 2007137335 A1 | 12/2007 |
| WO | 2007148231 A2 | 12/2007 |
| WO | 2008000045 A1 | 1/2008 |
| WO | 2008014234 A1 | 1/2008 |
| WO | 2008024149 A2 | 2/2008 |
| WO | 2008024511 A2 | 2/2008 |
| WO | 2008024511 A3 | 2/2008 |
| WO | 2008031144 A1 | 3/2008 |
| WO | 2008150974 A1 | 12/2008 |
| WO | 2009009487 A1 | 1/2009 |
| WO | 2009029866 A2 | 3/2009 |
| WO | 2009029866 A3 | 3/2009 |
| WO | 2009067764 A1 | 6/2009 |
| WO | 2009124042 A2 | 10/2009 |
| WO | 2009124042 A3 | 10/2009 |
| WO | 2009124042 A3 | 1/2010 |
| WO | 2010045432 A2 | 4/2010 |
| WO | 2010054281 A1 | 5/2010 |
| WO | 2010054308 A1 | 5/2010 |
| WO | 2010045432 A3 | 8/2010 |
| WO | 2011148316 A2 | 12/2011 |
| WO | 2011148317 A2 | 12/2011 |

OTHER PUBLICATIONS

Adrian A. Eshraghi et al, "D-JNKI-1 Treatment Prevents the Progression of Hearing Loss in a Model of Cochlear Implantation Trauma", Otology & Neurotology, Inc.; vol. 27, No. 4, 2006.

Review of Ophthalmology, www.revophth.com, "Present and Future Retinal Implants for chronic retinal conditions prone to recur, it might make sense to have an automatically recurring treatment, as well" Jobson Publishing LLC, Vol. No. 13:08Issue: Aug. 5, 2006.

Kha et al.; "Determination of frictional conditions between electrode array and endostrum lining for use in cochiear implant models"; Journal of Biomechanics; 2005; pp. 1752-1756; 39; Elsevier.

Plontke et al.; "Dexamethasone Concentration Gradients Along Scala Tympani After Application to the Round Window Membrane"; 2008; pp. 401-406; Otology & Neurotology. Inc.

James et al.: "Effects of Round Window Dexamethasone on Residual Hearing in a Guinea Pig Model of Cochlear Implantation"; Nov. 29, 2007; pp. 87-96; Audiology & Neurotology.

Laszig et al.; "Intracochlear insertion of electrodes using hyaluronic acid in cochlear implant surgery"; Oct. 15, 2001; pp. 371-372; Department of Otorhinolaryngology—Head and Neck Surgery; Freiburg; Germany; Department of Otolaryngology—Head and Neck Surgery; Haifa; Israel.

Dinh et al.; "Dexamethasone Protects Against TNF-Alpha Induced Loss of Auditory Hair Cells in Organ of Corti Explants by Altering the Expression Levels of Apoptosis-Associated Genes"; Feb. 17, 2008 (Abstract Only).

Eshraghi et al.; "Scala Tympani Infusion with Dexamethasone Base (DXMb) in Artificial Perilymph Protects Against Electrode Trauma-Induced Hearing"; Feb. 17, 2008 (Abstract Only).

Thomas R Van De Water et al, 10th International Conference on Cochlear Implants and Other Implantable Auditory Technologies, "Is a Drug Eluting Cochlear Implant Feasible and if so What is a Good Canidate Drug for the Conservation of Hearing"; Presentaion 26 p. 51; San Diego, California; Apr. 10, 2008.

Collaborative Research Center 599; "Subproject D2—Nerve-Electrode Interface"; Web page; http://www.mhh-hno.de/sfb599/tielprojekte/D2/d2_en.htm: Aug. 13, 2008.

Haake et al.; "Bioreleased Dexamethasone Can Prevent TNF-Alpha Induced Apoptosis of Auditory Hair Cells"; Feb. 17, 2008 (Abstract Only).

Vivero et al.; "Dexamethasone Base Conserves Hearing from Electrode Trauma-Induced Hearing Loss"; pp. 1-8; Article; The American Laryngological, Rhinological and Otological Society, Inc.; Jun. 26, 2008.

Eshrangi et al.; "Local Dexamethasone Therapy Conserves Hearing in an Animal Model of Electrode Insertion Trauma-Induced Hearing Loss"; Otology & Neurotology: Sep. 2007—vol. 28—Issue 6—pp. 842-849 Otology & Neurotology, Inc.

Vivero et al.; "Dexamethasone Preserves Hearing during Cochlear Implantation"; Aug. 1, 2007; pp. 190-191; vol. 137; No. 2S; Otolaryngology—Head and Neck Surgery.

Huang et al."Effects of steroids and lubricants on electrical impedance and tissue response following cochlear implantation"; Cochlear Implants International Sep. 14, 2007, vol. 8; No. 3, pp. 123-147.

* cited by examiner

MINIMIZING TRAUMA DURING AND AFTER INSERTION OF A COCHLEAR LEAD

RELATED APPLICATIONS

The present application claims priority under 35 U.S.C. §119(e) to U.S. Provisional Patent Application No. 60/968,785, by Edward H. Overstreet et al., filed on Aug. 29, 2007, and entitled "Drug Loaded Lubricant for the Purposes of Minimizing Trauma During Insertion & Post Insertion of a Cochlear Lead," the contents of which are hereby incorporated by reference in its entirety.

BACKGROUND

A cochlear implant is a surgically implanted electronic device that resides in the cochlea of a patient's ear and provides a sense of sound to the patient who is profoundly deaf or severely hard of hearing. The present specification relates to such neural stimulators and, particularly, to cochlear implant systems that include electrode arrays for stimulation of a patient's cochlea. In a typical cochlear implant, an array of electrode contacts are placed along one side of an elongate carrier or lead so that when the array is implanted within one of the cochlear ducts, such as the scala tympani, the electrode contacts are positioned in close proximity to the cells that are to be stimulated. This allows such cells to be stimulated with minimal power consumption.

To maximize the benefit of the surgery for the patient, it is important to preserve the residual hearing of the patient and to maximize the long term effectiveness of the cochlear implant. As the cochlear lead is inserted through the tissues in the head and into the cochlea, there can be mechanical damage to the surrounding tissues, subsequent inflammation, and possibly damage to the delicate structures within the cochlea. Additionally, various autoimmune reactions can occur in response to the presence of the cochlear lead in the cochlea. These autoimmune reactions can include growth of tissue around the cochlear implant and eventual ossification. This tissue growth can act as a barrier between the electrodes of the cochlear implant and the target nerves. This can lead to a degradation of the performance of the cochlear implant over time.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Figure 1:
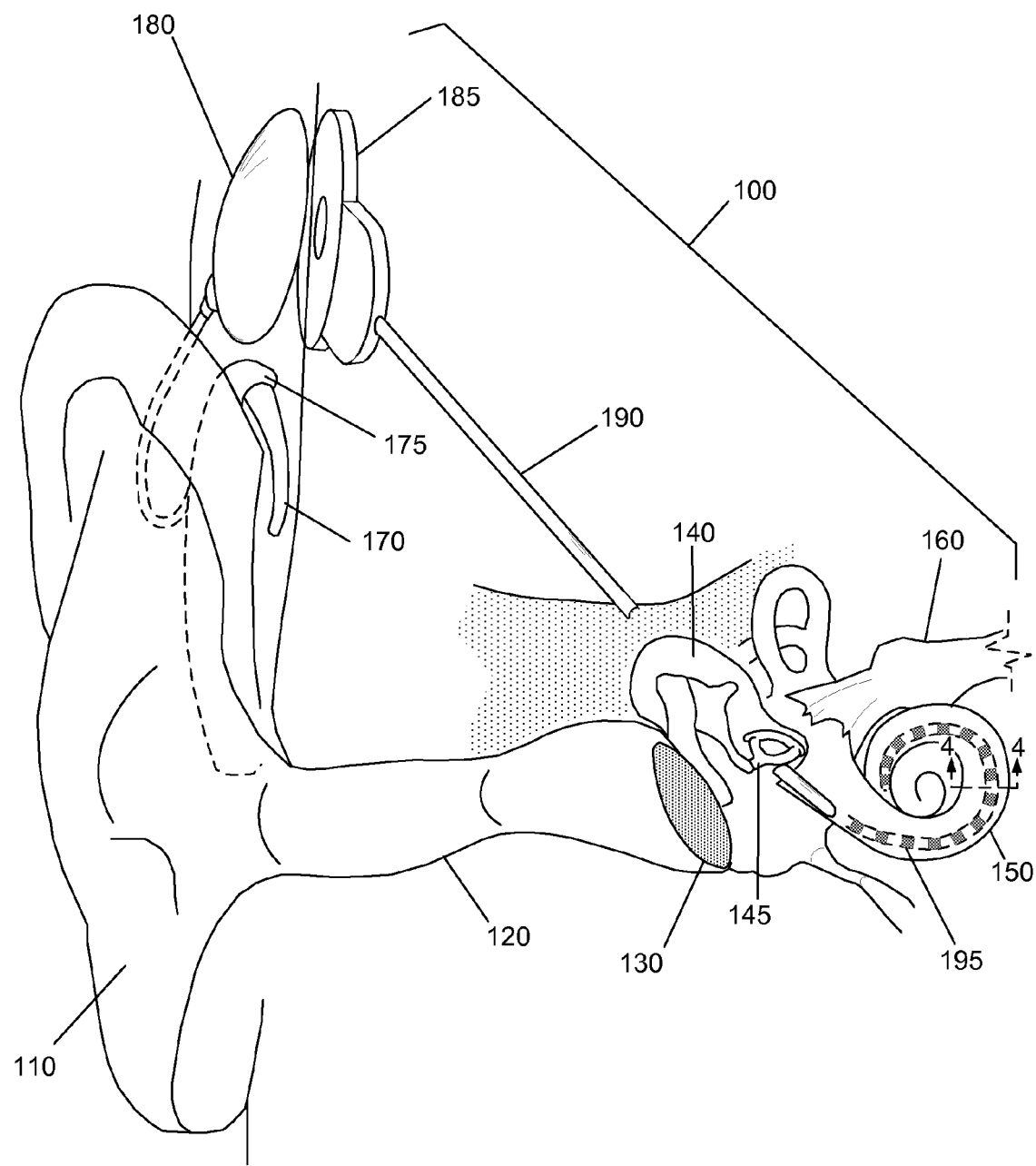
FIG. 1 is diagram showing an illustrative cochlear implant that is surgically placed within the human anatomy, according to one embodiment of principles described herein.

To place a cochlear implant, the terminal portion of a cochlear lead is pushed through an opening into the cochlea. The terminal portion of the lead is typically constructed out of biocompatible silicone. This gives the terminal portion of the lead the flexibility to curve around the helical interior of the cochlea. However, silicone has a high coefficient of friction and requires that a relatively high axial force be applied along the cochlear lead during the insertion process. As a result, the silicone can mechanically abrade or otherwise damage the interior of the cochlea, which can cause inflammation and disturbance of the vestibular duct or other structures, leading to nerve damage, vertigo, and/or tinnitus.

Additionally autoimmune reactions can cause nerve damage and undesirable tissue growth within the cochlea. The presence of the cochlear lead, an object foreign to the body, can activate macrophages. This typically occurs approximately three days after implantation of the cochlear lead. Once activated, the macrophages attach themselves to the surface of the electrode and form multi-nucleated giant cells. These cells, in turn, secrete various substances, such a hydrogen peroxide, as well as various enzymes, in an effort to dissolve the foreign object. Such substances, while intending to dissolve the foreign object, also inflict damage to the surrounding tissue and nerves. These substances can cause necrosis of a portion the surrounding hair cells and spiral ganglions. The necrosis of these cells can cause a loss of residual hearing and reduce the effectiveness of the cochlea in converting electrical impulses generated by the cochlear lead into auditory nerve signals. Consequently, there can be a need for increased electrical stimulation to obtain satisfactory results. Even after the microscopic areas of tissue die, the inflammatory response continues and approximately seven days after implant the multi-nucleated giant cells cause fibroblasts to begin laying down collagen. This can result in the encapsulation of the cochlear lead by a layer of fibrotic tissue, which insulates the cochlear lead from the remaining nerve cells and further reduces the effectiveness of applied voltages.

As a consequence of this potential for damage to the residual hearing of a patient and reduction of efficiency of the cochlear lead over time, the majority of patients who are considered for cochlear implants have severe or total hearing loss. For this of group patients, the benefits provided by the cochlear implant can outweigh the risk of residual hearing loss. However, by solving the problems described above, cochlear implants could improve the hearing and quality of life of a much broader range of patients. Particularly, as a surgeon's ability to conserve residual hearing increases, the potential to implant patients with greater levels of baseline hearing can become a reality.

The initial mechanical tissue damage caused during the insertion of the cochlear lead can be significantly reduced by minimizing the coefficient of friction between the silicone and the body tissues. The coefficient of friction can be minimized by applying a lubricant to the outer surface of the silicone cochlear lead. However, the outer surface of the silicone is smooth and hydrophobic, which prevents the uniform and permanent application of a biocompatible lubricant. This issue can be addressed by altering the chemical characteristics of the exterior of the silicone. Then, a variety of lubricants can be coated onto the lead.

In addition to the need to reduce the mechanical damage caused by the insertion of the cochlear lead, the administration of various therapeutic drugs within the cochlea can minimize the biological reactions to the surgery and presence of a foreign body. The natural inflammation and immune system responses to the insertion of the cochlear lead can be reduced by the proper application of drugs intended to counter thrombus, fibrosis, inflammation, and other negative reactions. Additionally, other drugs could be applied to prevent infection, encourage the growth or regeneration of nerve cells, or other desirable effects. Ideally, a comparatively large dose of steroid or other appropriate drug or drug combination would be administered during or shortly after implantation of the cochlear lead. Following this initial dose, a lower, long-duration dose could be administered to prevent or reduce undesirable autoimmune system responses.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

For purposes of clarity, as used herein, an implantable stimulating lead is a device that has one or more electrode contacts that deliver current to tissue to be stimulated. An electrode contact is that part of the stimulating device which is actually electrically conductive and is in contact with the body tissue that is to be stimulated.

In the art, the term "electrode" may sometimes be used narrowly to refer to the electrode contact or contacts only and, at other times, more broadly, to refer to the electrode contact or contacts and all the surrounding structure, including the insulation carrier that the contacts are placed on as well as the conductor wires and any other assemblies within or on the insulation carrier. As used herein, the broad definition of the term "electrode" will be adopted, which includes the electrode contacts and all surrounding structures. In addition, when the term "lead" is used, it will be used interchangeably with the broad use of the term "electrode."

The term "electrode array" will refer to that portion of the electrode, or lead, that includes all of the electrode contacts and the immediate structures upon which the electrode contacts are attached. Thus, the term "electrode array" may be narrower than the broad term "electrode" in that any carrier insulation and conductor wire that is not immediate to the electrode contacts will not be included in the term "electrode array."

Hearing loss, which may be due to many different causes, is generally of two types: conductive and sensorineural. Of these, conductive hearing loss occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also amenable to alleviation by surgical procedures.

In many people who are profoundly deaf, however, the reason for their deafness is sensorineural hearing loss. This type of hearing loss can arise from the absence or the destruction of the hair cells in the cochlea which transduce acoustic signals into auditory nerve impulses. Individuals with sensorineural hearing loss are unable to derive any benefit from conventional hearing aid systems no matter how loud the acoustic stimulus is, because the mechanism for transducing sound energy into auditory nerve impulses has been damaged. Thus, in the absence of properly functioning hair cells, auditory nerve impulses cannot be generated directly from sound waves.

To overcome sensorineural deafness, cochlear implant systems or cochlear prostheses have been developed that bypass the hair cells, which normally transduce acoustic energy into electrical impulses by direct electrical stimulation of the auditory nerve cells. This leads to the perception of sound in the brain and provides at least partial restoration of hearing function. Thus, most of these cochlear prosthesis systems treat sensorineural deficit by stimulating the ganglion cells in the cochlea directly using an implanted electrode or lead that has an electrode array.

In addition to stimulating the nerve cells, the electronic circuitry and the electrode array of the cochlear prosthesis separate the acoustic signal into a number of parallel channels of information, each representing a narrow band of frequencies within the perceived audio spectrum. Ideally, each channel of information should be conveyed selectively to a subset of auditory nerve cells that normally transmits information about that frequency band to the brain. Those nerve cells are arranged in an orderly tonotopic sequence, from the highest frequencies at the basal end of the cochlear spiral to progressively lower frequencies towards the apex.

Electrical stimulation of predetermined locations within the cochlea of the human ear through an intracochlear electrode array is described, e.g., in U.S. Pat. No. 4,400,590 (the "'590 patent"), which is incorporated herein by reference. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,605, which is incorporated herein by reference. The system described in the '590 patent receives audio signals, i.e., sound waves, at a signal processor (or speech processor) located outside the body of a hearing impaired patient. The speech processor converts the received audio signals into modulated radio frequency (RF) data signals that are transmitted through the patient's skin and then by a cable connection to an implanted multi-channel intracochlear electrode array. The modulated RF signals are demodulated into analog signals and are applied to selected contacts of the plurality of exposed electrode pairs in the intracochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

Over the past several years, a consensus has generally emerged that the scala tympani, one of the three parallel ducts that make up the spiral-shaped cochlea, provides the best location for implantation of an electrode array used as part of a cochlear prosthesis. The electrode array to be implanted in the scala tympani typically consists of a thin, elongated, flexible carrier containing several longitudinally disposed and separately connected stimulating electrode contacts, conventionally numbering about 6 to 30. Such an electrode array is pushed into the scala tympani duct in the cochlea to a depth of about 20-30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site. Thus, it is important generally for the electrode contacts to be positioned as close to the ganglion cells as possible. Conventionally, after implant, the electrode array consisting of electrode contacts should hug the modiolar wall (or inside wall of the scala tympani), without causing undue pressure. When the electrode side of the array is positioned closest to the modiolar wall, the electrode contacts are on the medial side of the lead.

In order to address the above need, it is known in the art to make an intracochlear electrode array that includes a spiral-shaped, resilient carrier which generally has a natural, spiral shape so that the array better conforms to the shape of the scala tympani. See, e.g., U.S. Pat. No. 4,819,647, which is incorporated herein by reference. While the electrode array with a spiral-shaped carrier shown in the '647 patent represents a significant advance in the art, it lacks sufficient shape memory to allow it to return to its original curvature (once having been straightened for initial insertion) and to provide sufficient hugging force to wrap snugly against the modiolus of the cochlea.

It is also known in the art, as shown in U.S. Pat. Nos. 5,545,219 and 5,645,585, to construct an electrode carrier from two initially straight members, a rod-like electrode carrier and a flexible rod-like positioning member. The '219 and '585 U.S. patents are also incorporated herein by reference. As shown in these patents, the two members extend in substantially parallel relation to and closely alongside each other, but are connected to each other only at their respective leading and trailing ends. After implant, a pushing force is applied to the positioning member so that it is forced to assume an outwardly arched configuration relative to the electrode carrier, thereby forcing the electrode carrier into a close hugging engagement with the modiolus and placing the electrode contacts as close to the cells of the spiral ganglion as possible. The '219 patent, in particular, shows in FIGS. 1-10 and describes in the accompanying text an excellent summary of prior art electrodes and the deficiencies associated therewith.

Other patents relevant to the subject matter of cochlear stimulation leads are: U.S. Pat. Nos. 6,125,302; 6,070,105; 6,038,484; 6,144,883; and 6,119,044, which are all herein incorporated by reference. Other improved features of cochlear implant systems are taught, e.g., in U.S. Pat. Nos. 6,129,753; 5,626,629; 6,067,474; 6,157,861; 6,249,704; and 6,289,247, each of which is incorporated herein by reference.

While the electrode arrays taught in the above-referenced patents are based on the correct goal, i.e., to force the electrode carrier into a close hugging engagement with the modiolus, they do so only by using an additional element that makes manufacture of the lead more difficult and expensive and only by applying an additional pushing force to an electrode structure after it has already been inserted into the cochlea. Such additional pushing force may cause damage to the delicate scala tympani or cause the electrode contacts to twist or to separate away from the modiolus, rather than be placed in the desired hugging relationship. Thus, while it has long been known that an enhanced performance of a cochlear electrode or lead can be achieved by proper placement of the electrode contacts close to the modiolar wall of the cochlea, a major challenge has been obtaining an electrode/lead design that does not require excessive force to achieve this close placement. According to one illustrative embodiment, the surface of the cochlear lead is modified to allow a lubricant to uniformly cover the cochlear lead and minimize the insertion forces and resulting trauma.

Additionally, the cochlear implant can be used as a vehicle for carrying therapeutic substances, such as steroids and anti-bacterial drugs, directly to disturbed tissues within the cochlea. A variety of delivery mechanisms can be used to deliver the drug or combination of drugs. A number of patents relate to manufacturing methods and drug delivery by implantable leads, including: U.S. Pat. No. 4,506,680 (a drug impregnated silicone plug retained within a cavity in an implantable lead); U.S. Pat. No. 5,092,332 (a drug impregnated polymeric layer bonded to an implantable lead); U.S. Pat. No. 5,103,837 (an implantable lead with a porous outer surface that contains an anti-inflammatory steroid), U.S. Pat. No. 5,609,029 (a cochlear implant with a drug impregnated outer coating); U.S. Pat. No. 5,496,360 (an implantable lead having a central cavity configured to receive various drug products); U.S. Pat. No. 5,824,049 (a manufacturing method for applying a drug layer covered by porous layer of biocompatible polymer to an implantable lead); U.S. Pat. No. 5,987,746 (an implantable lead being coated with a drug which is no more than sparingly soluble in water); U.S. Pat. No. 6,259,951 (an implantable cochlear lead which uses both electrode and displacement stimulation); U.S. Pat. No. 6,304,787 (a cochlear lead treated with a drug compound); U.S. Pat. No. 6,862,805 (a manufacturing method for a cochlear implant); U.S. Pat. No. 6,879,695 (a personal audio system with an implanted wireless receiver/audio transducer); U.S. Pat. No. 7,187,981 (an implantable lead with a lubrication/drug eluting coating); U.S. Pat. No. 7,294,345 (a generic method for biological delivery of drug compounds into a matrix); and U.S. Pat. No. 7,363,091 (an implantable lead containing a silicone elastomer matrix containing steroids); U.S. App. Nos.: 20070213799 (cochlear electrode arrays with drug eluting portions); 20060282123 (medical devices resistant to tissue overgrowth); 20060287689 (cochlear implants configured for drug delivery); and 20080014244 (polymer matrix for containing therapeutic drugs); European Pat. No.: EP0747069 (a manufacturing method for applying a drug layer covered by porous layer of biocompatible polymer to an implantable lead); PCT Publication Nos. WO2008/024511 (layered matrix impregnated with therapeutic drugs) and WO2008/014234 (a cochlear implant with a drug eluting polymer material); which are all herein incorporated by reference. These patents describe a number of manufacturing techniques which can be utilized in conjunction various illustrative embodiments of cochlear implants which are described below.

According to one illustrative embodiment, the drugs may be coated on the outer surface of the implant, with the thickness and surface area of the various layers corresponding to the desired delivery drug profile and dose. In another embodiment, the drugs may also be encapsulated in a matrix which gradually releases the drugs into the intracochlear space. This matrix may be attached to cochlear lead in a variety of ways, including as a coating, a plug, or other geometry. In another illustrative embodiment, the drugs could also be delivered as a powder that is contained within a cavity of the implant. The drug type, particle size, cavity opening, covering membrane or other means could be used to control the delivery of the drug. However, in all cases, the amount of drug delivered is constrained by the need to minimize the size of the intracochlear lead. Any increase in the size of the intracochlear lead increases the potential for mechanical damage and disruption to the cochlea. Thus, a selection of the most efficacious drug or combination of drugs is important, given that only a small quantity of the drugs can be delivered via the intracochlear lead.

As mentioned above, and by various incorporated references, a variety of drugs or drug combinations could be beneficial for a patient receiving a cochlear implant. In the past, one of the primary considerations in selecting drugs for administration on electrical nerve stimulation implants (such as vagus nerve stimulators, pace makers, cochlear leads, etc.) was that the drugs should have a high solubility in aqueous solutions. The majority of the fluids within the human body contain a high percentage of water, and thus serve as an aqueous solution capable of acting as a solvent for the drugs. However, the applicants have discovered that dexamethasone base (DXMb), which has a very low solubility in aqueous solutions, was surprisingly efficacious when administered into the intracochlear space after implantation surgeries. Additionally, DXMb was surprisingly more potent than salt forms of dexamethasone. This surprising potency allows for increased therapeutic effects without increasing the volume of the drug or the size of the intracochlear lead.

FIG. 1 is a diagram showing one illustrative embodiment of a cochlear implant (100) surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third of the ossicles, or stirrup, (145) contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. As also noted above, in many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from sensorineural hearing loss.

Unlike hearing aids, the cochlear implant (100) does not amplify sound, but works by directly stimulating any functioning auditory nerve cells inside the cochlea (150) with electrical impulses. Cochlear prosthesis typically involves the implantation of electrodes into the cochlea. The cochlear prosthesis operates by direct electrical stimulation of the auditory nerve cells, bypassing the defective cochlear hair cells that normally traduce acoustic energy into electrical energy.

External components of the cochlear implant include a microphone (170), speech processor (175), and transmitter (180). The microphone (170) picks up sound from the environment and converts it into electrical impulses. The speech processor (175) selectively filters and manipulates the electrical impulses and sends the processed electrical signals through a cable to the transmitter (180). The transmitter (180) receives the processed electrical signals from the processor (175) and transmits them to the receiver (185) by electromagnetic induction and/or by using radio frequencies.

In some cochlear implants, the transmitter (180) is held in place by a magnetic interaction with the underlying receiver (185). The receiver (185) is secured beneath the user's skin, typically above and behind the external ear (110). The receiver (185) sends the signals through the cochlear lead (190) to the electrodes (195). The electrodes (195) are wound through the cochlea (150) and provide direct electrical stimulation to the auditory nerve inside the cochlea (150).

The implant works by using the tonotopic organization of the basilar membrane of the inner ear. The tonotopic organization, also referred to as "frequency-to-place" mapping, is the way the ear differentiates between sounds of different frequencies. In a normal ear, sound vibrations in the air are converted into resonant vibrations of the liquid within the cochlea. High-frequency sounds do not pass very far through the liquid and the structures of the cochlea that contain the liquid. Low-frequency sounds pass farther down the cochlear channels. Consequently, the nerve cells at the basal end of the cochlear spiral sense higher frequencies, while progressively lower frequencies are sensed at different portions of the cochlear spiral moving towards the apex. The movement of hair cells located all along the basilar membrane stimulates the surrounding nerve cells which conduct electrical impulses to the brain. The brain is able to interpret the nerve activity to determine which area of the basilar membrane is resonating and, therefore, what sound frequencies are being heard.

For individuals with sensorineural hearing loss, hair cells are often fewer in number and/or damaged. The cochlear implant bypasses the hair cells and stimulates the cochlear nerves directly using electrical impulses. The cochlear implant stimulates different portions of the cochlea (150) according to the frequency detected by the receiver (185), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
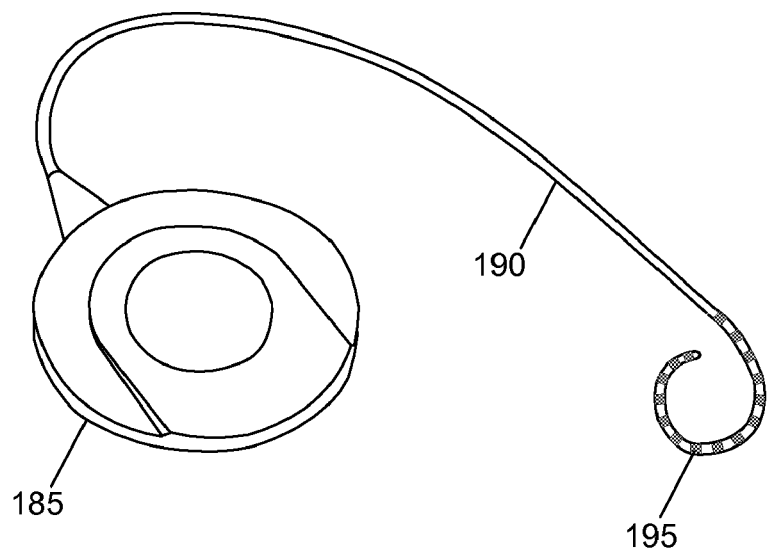
FIG. 2 is a perspective view of an illustrative cochlear implant device, according to one embodiment of principles described herein.

FIG. 2 shows one illustrative embodiment of the internal components of the cochlear implant device. The receiver (185) is connected to the cochlear lead (190) which terminates in a flexible end that contains the electrodes (195). The electrodes (195) consist of a plurality of individual electrodes contacts made from platinum or at a similarly high conductive material. These electrodes and associated wires are supported and connected by a flexible and durable biocompatible material, typically silicone rubber.

Figure 3:
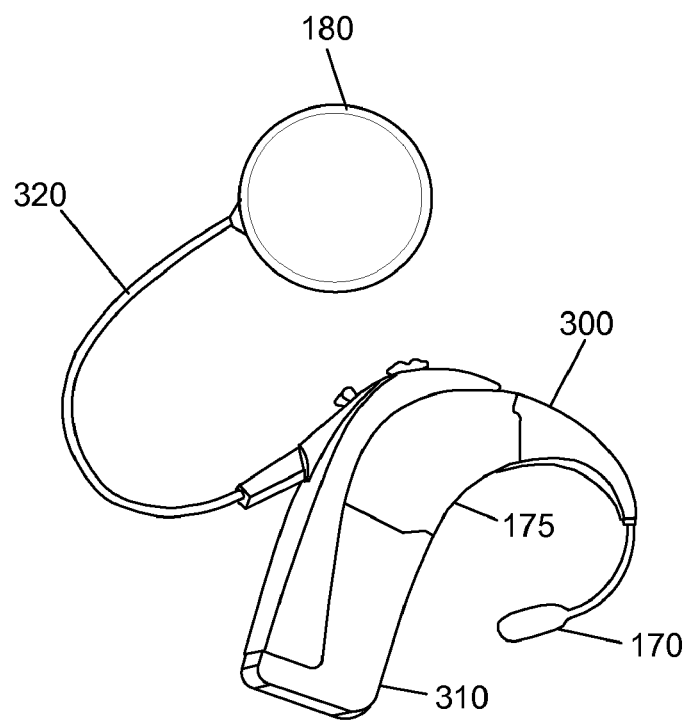
FIG. 3 is a perspective view of an illustrative external portion of the cochlear implant device, according to one embodiment of principles described herein.

FIG. 3 shows one illustrative embodiment of the external components of the cochlear implant. The microphone (170) is attached to the ear hook (300). The ear hook (300) secures the external components behind the outer ear. The microphone (170) senses environmental sounds and converts those sounds into electrical impulses. The processor (175) filters and manipulates the electrical impulses it receives from the microphone (170) and transmits processed electrical sound signals along the external cable (320) to the transmitter (180). The processor (175), microphone (170) and transmitter (180) are powered by a battery (310).

Figure 4:
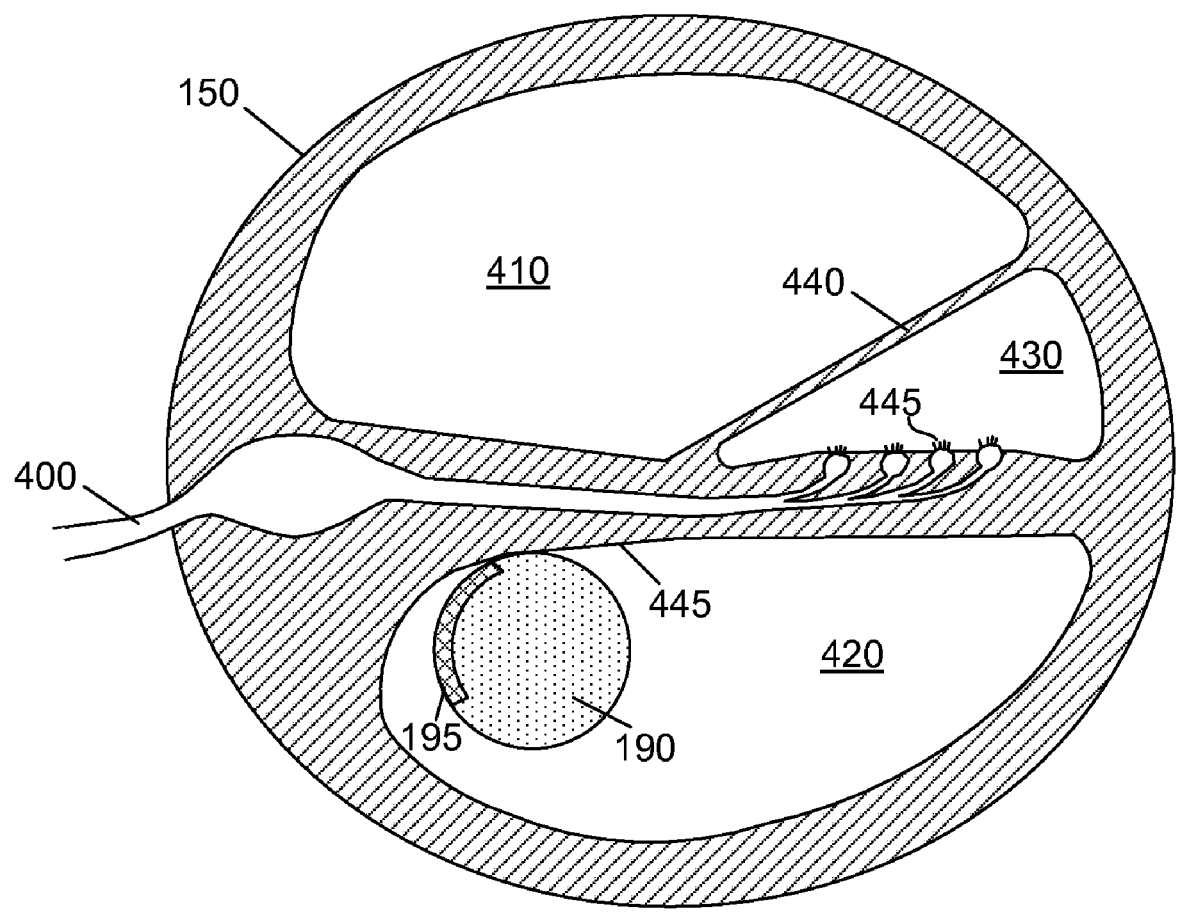
FIG. 4 is an illustrative cross-sectional diagram of the cochlea showing the insertion location of the intra cochlear lead, according to one embodiment of principles described herein.

FIG. 4 shows a cross sectional diagram of the cochlea (150) taken along line 4-4 in FIG. 1. The walls of the hollow cochlea (150) are made of bone, with a thin, delicate lining of epithelial tissue. The primary structure of the cochlea is a hollow tube that is helically coiled, similar to a snail shell. The coiled tube is divided through most of its length by the basilar membrane (445). Two fluid-filled spaces (scalae) are formed by this dividing membrane (445). The scala vestibuli (410) lies superior to the cochlear duct. The scala tympani (420) lies inferior to the scala cochlear duct. The scala media (430) is partitioned from the scala vestibuli (410) by Reissner's membrane (440).

The cochlea (150) is filled with a watery liquid, which moves in response to the vibrations coming from the middle ear via the stirrup (145). As the fluid moves, thousands of "hair cells" (445) in a normal, functioning cochlea are set in motion and convert that motion to electrical signals that are communicated via neurotransmitters to many thousands of nerve cells (400). These primary auditory neurons (400) transform the signals into electrical impulses known as action potentials, which travel along the auditory nerve to structures in the brainstem for further processing. The terminal end of the cochlear lead (190) is inserted into the scala tympani with the electrodes (195) preferably being positioned in close proximity to the nerve (400).

Figure 5:
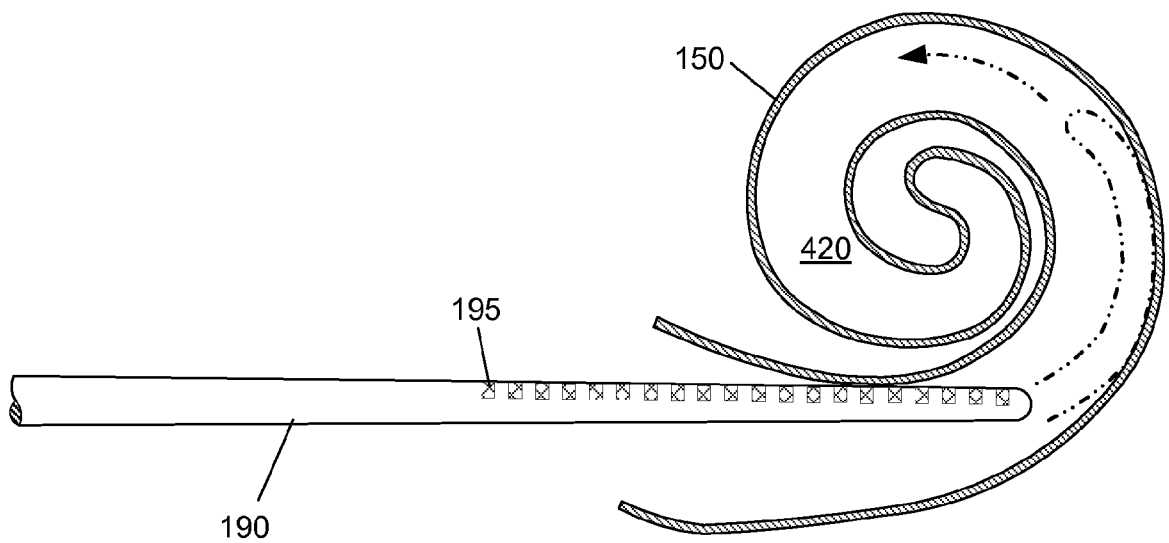
FIG. 5 is an illustrative diagram of the insertion of the terminal portion of an intra cochlear lead into the cochlea, according to one embodiment of principles described herein.

As shown in FIG. 5, the tip of the cochlear lead (190) is inserted through an incision in the cochlea (150) and pushed into the scala tympani (420) so that the tip of the lead conforms to the helical shape of the scala tympani. A major problem with electrode insertion is potential damage to the delicate structures within the cochlea. To insert the cochlear lead, a passageway is made through the body tissues of the head to expose the cochlea. The tip of the electrode is inserted through an opening in the cochlea. The electrode is then pushed axially into the cochlea. The force of the tip against the inner wall of the cochlear channel bends the flexible tip. When the tip is in its final position, the electrode array is entirely contained within the cochlea and the individual electrodes (195) are placed proximate the nerve cells (400). When electrical current is routed into an intracochlear electrode (195), an electric field is generated and the auditory nerve fibers (400, FIG. 4) are selectively stimulated.

Many surgeons, in an off-label practice, apply a lubricant HEALON hyaluronic acid (Pharmacia Corporation, Peapack, N.J., USA) to the electrode array to decrease the friction between the cochlear implant lead and the patient's internal tissues. However, HEALON lubricant is highly viscous and when applied at the time of surgery, there is little or no control over the conformity of the coating across the silicone surface.

According to one illustrative embodiment, a pre-coated cochlear lead can be used to ensure the desired amount of surface area is coated with a uniform and reliable lubricant. Increasing lubricity of the silicone in the cochlear implant lead will help to reduce the probability that the soft tissues of the cochlear will be torn upon electrode insertion and make the insertion of leads much easier.

Figure 6:
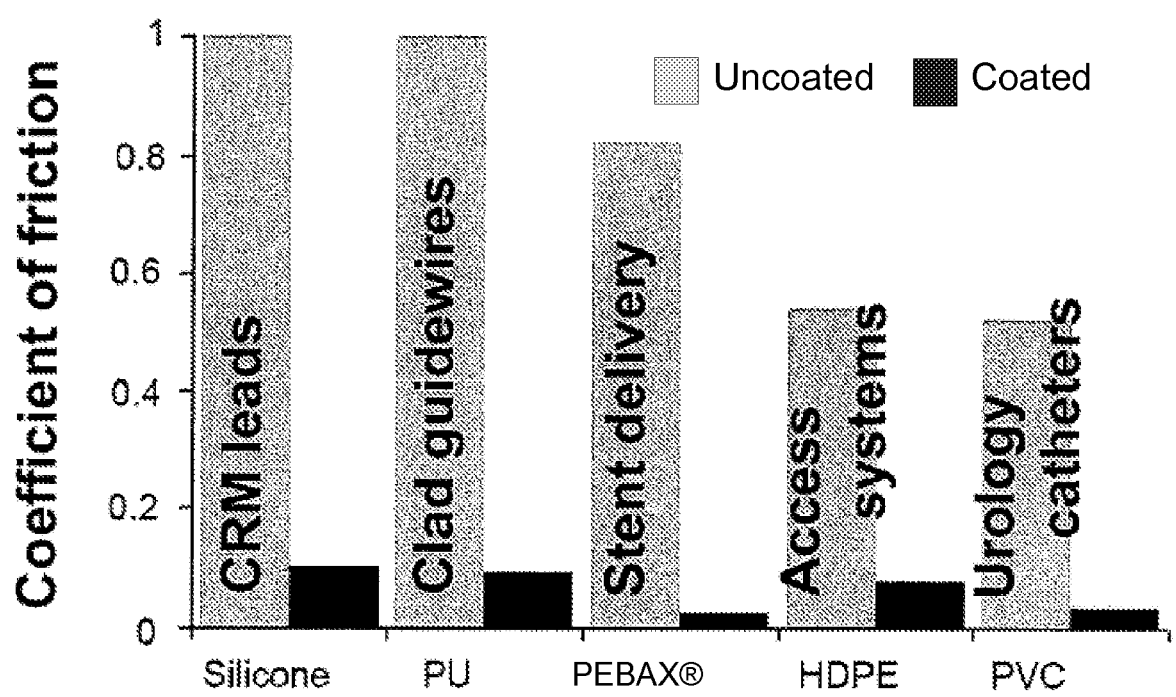
FIG. 6 an illustrative diagram of representative coefficients of friction for various coatings commonly used on surgical devices, according to one embodiment of principles described herein.

FIG. 6 shows experimental results of tests performed with various materials that are used as the outer surfaces of medical devices. The vertical axis shows the range of the coefficient of friction. The horizontal axis shows various materials that were tested. For example, uncoated silicone cardiac rhythm management (CRM) leads had a coefficient of friction of approximately 1. After a hydrophilic lubricious coating was applied to the silicone, the coefficient of friction was reduced to approximately 0.1. Thus, the use of a lubricious coating may reduce friction forces by 90% or more as shown in FIG. 6 on various surfaces, including silicone as used in the cochlear lead's electrode array.

Silicone is known to be an unreactive polymer. It has a very low surface energy and is wettable by few liquids. Therefore, it is difficult to attach molecules or coatings to its surfaces. Its surfaces can be made wettable and hydrophilic by subjecting the silicone to oxygen plasma. This introduces hydroxyl groups on the exposed silicone surfaces. However, these wetting and hydrophilic properties are temporary. Silicone undergoes rapid surface inversion and reverts back to a hydrophobic and unwettable material within 24 hours.

However, within the time immediately after treatment of the silicone with oxygen plasma, these temporary hydroxyl groups may be utilized to attach coatings or to derivatize the surface. Examples of reactive molecules that could be used to modify the surface include Propyltrimethoxysilane ($C_3H_7$—$Si(OCH_3)_3$), Glycidoxypropyltrimethoxysilane ($CH_2(O)CHCH_2OC_3H_6$—$Si(OCH_3)_3$), Aminopropyltriethoxysilane ($H_2NC_3H_6$—$Si(OC_2H_5)_3$), Aminoethylaminopropyltrimethoxysilane ($H_2NC_2H_4NHC_3H_6$—Si($OCH_3$)$_3$), Methacryloxypropyltrimethoxysilane ($H_2C$=CH($CH_3$)C(O)O$C_3H_6$—Si($OCH_3$)$_3$), Mercaptopropyltrimethoxysilane (HS($CH_2$)$_3$Si(OMe)$_3$), Chloropropyltrimethoxysilane (Cl$C_3H_6$—Si($OCH_3$)), Phenyltrimethoxysilane ($C_6H_5$—Si($OCH_3$)$_3$), and Vinyltrimethoxysilane ($H_2C$=CH—Si($OCH_3$)$_3$). All of these compounds can react permanently with the hydroxyl groups through a covalent linkage via a silyl ether linkage. These alkoxy silanes have been added to lattices and hydrolyzed to form an interpenetrating polymer network (IPN) polymer with improved properties.

Two types of alkoxy silanes have widespread application in the coatings industries: alkyl/aryl and organofunctional. Possessing both organic and inorganic properties, these hybrid chemicals react with the polymer, forming durable covalent bonds across the interface. It has been proposed that these bonds are hydrolyzable, but can reform, and therefore provide a means of stress relaxation at the organic/inorganic interface. The results are improved adhesion and durability.

Figure 7:
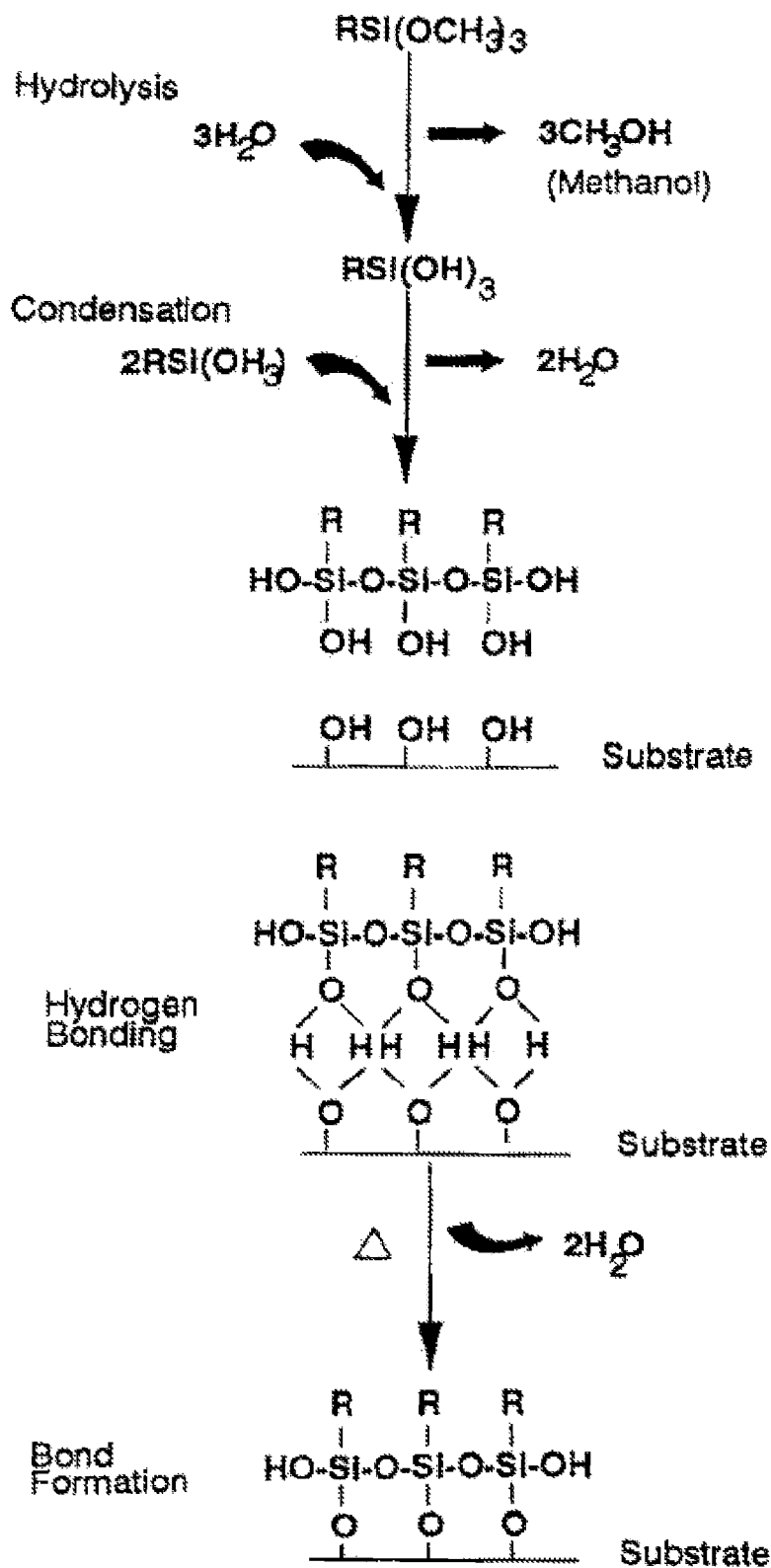
FIG. 7 is an illustrative diagram illustrating a series of chemical reactions of silanes with silicone, according to one embodiment of the principles described herein.

FIG. 7 shows a diagram of the reaction of silanes to enhance bonding with a substrate. Initially, hydrolysis of the alkoxy groups occurs. It is after the first and second alkoxy groups are hydrolyzed that condensation to oligomers follows. The tendency toward self condensation can be controlled by using fresh solutions, alcoholic solvents, dilution, and by careful selection of pH ranges. The third methoxy group upon hydrolysis is oriented towards and hydrogen bonds with the hydroxyl groups on the silicone surface. Finally, during curing (110° C./10 min) a covalent bond is formed with the silicone, water is liberated and the interpenetrating network is formed improving the mechanical strength and preventing surface inversion of the silicone.

The most straightforward method of silylating a surface with a silane is from an alcohol solution. A two percent silane solution can be prepared in the alcohol of choice (methanol, ethanol, and isopropanol are typical choices). The solution can be wiped, dipped, or sprayed onto the surface. After the surface dries, excess material can be gently wiped, or briefly (alcohol) rinsed off. Cure of the silane layer is for 5-10 minutes at 110° C. or for 24 hours at ambient conditions.

The resulting additives change the surface energy of the silicone polymer (e.g., more lubricious and wettable) and makes the silicone surface much more reactive for subsequent reactions. For example, if the silicone were treated with Methacryloxypropyltrimethoxysilane, $H_2C$=CH($CH_3$)C(O)O$C_3H_6$—Si($OCH_3$)$_3$, it would have a free vinyl group which could subsequently be used to react with a hydrophilic vinyl containing monomer, oligomer, or polymer, forming a covalent bond by free radical reaction. This hydrophilic coating would render the silicone not only lubricious but also able to imbibe drugs for subsequent drug delivery.

As described above, one method of precisely delivering the steroid is to impregnate the chemically modified silicone of the cochlear implant lead with the steroid. The steroid leaches out of the porous silicone over time, creating a time release mechanism for delivering the steroid directly the tissue affected by the implantation of the lead.

Figure 8:
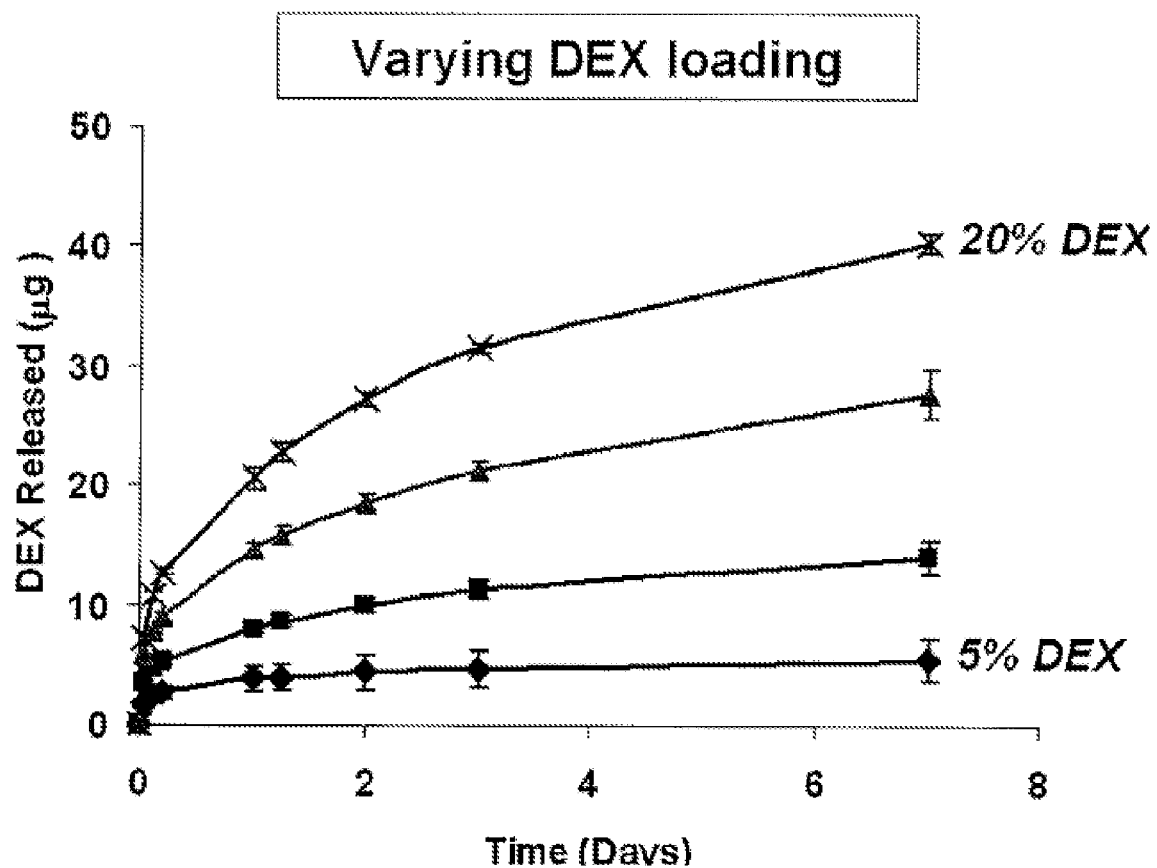
FIG. 8 is an illustrative chart showing the release of a steroid from a polymer coating, according to one embodiment of principles described herein.

FIG. 8 shows the drug elution of a steroid DEX salt from the polystyrene-polyisobutylene-polystyrene (SIBS) polymer coating. SIBS is an elastomeric block copolymer of polystyrene and polyisobutylene used for medical applications such as stent coatings. The vertical axis shows the total amount of DEX salt released in micrograms. The horizontal axis shows elapsed time in days. The test shows the advantageous release of large quantities of steroid immediately following the insertion of the surgical device. As the tissues heal over a period of time, the need for steroid intervention decreases. The elution profiles shown in FIG. 8 show a corresponding reduction in the rate of steroid elution over a period of days. The elution profile can be chosen to match the needs of the patient by increasing or decrease the percentage of DEX salt in the SIBS polymer.

In one alternative embodiment, the steroid is delivered in combination with lubrication. A lubricant containing a steroid substance is applied along the length in part or in whole to the cochlear lead to minimize trauma to the cochlea. The lubricant will allow the lead to be more easily inserted by reducing frictional forces that can tear soft tissues. During insertion and post insertion of the lead, the steroid substance will diffuse into the surrounding tissues and reduce the initial trauma and subsequent inflammation that the cochlea and other tissues may experience. Minimizing inflammatory processes during and after the insertion of the cochlear lead can increase the probability of preserving residual hearing.

A class of lubricants referred to as "slippery when wet" lubricants have the characteristic of being applied, packaged, and transported as a dry powder or dry coating. Prior to insertion, the coated article is immersed or otherwise brought into contact with an aqueous solution (typically purified water or saline solution). The dry powder absorbs the solution and becomes lubricious. As the coated object is inserted into tissue, it further absorbs body fluids to enhance its low friction characteristics.

In embodiments using "slippery when wet" lubricants where the steroid is to be combined with the lubricant, the "slippery when wet" lubricant powder or dry coating is brought into contact with a steroid solution. The lubricant coating absorbs the steroid and delivers it to tissues that the coated object encounters. The steroid could also be coated directly on the silicone as part of the lubricious coating. The lubricious coating consists of one- or multiple-layer polymer coatings bound to the silicone. In the case that multiple coatings are used, the base coating may provide excellent adhesion to the silicone substrate while also containing the steroid. The top coating may provide the improved lubricity to ease the surgical implantation of the cochlear implant lead.

In these exemplary embodiments, a variety of commercially available lubricious coatings could be used. By way of example and not limitation, the following lubricants could be used: LUBRILAST from AST Products, HARMONY from SurModics, SILGLIDE from Applied Membrane Technology, HYDAK from Biocoat, F2 series from Hydromer, and others.

The lubricious coating can be applied to the lead using any of a number of techniques. For example, the lubricious coating can be applied by means of dip coating, spray coating, electro-deposition, direct printing (such as with ink-jet technology) or brush painting.

In another exemplary embodiment, the steroid could be encased in a vesicle, such as a nanoparticle or liposome vesicle, or combined with a biodegradable substance to facilitate time release. Nanoparticles and liposomes could be suspended in the lubricious coating or contained within porous coatings. In addition to the benefits described above, the polymer coating on cochlear leads may provide additional valuable characteristics such as anti-microbial, anti-thrombogenic and reduced fibrosis.

Alternative lubricants include a hydrophilic polymeric material such as plant- and animal derived natural water-soluble polymers, semi-synthetic water-soluble polymers, and synthetic water-soluble polymers. Further, the water-soluble polymers are can be stabilized (turned to be water-insoluble) by such means as crosslinking. Specific examples of the hydrophilic polymeric material include polyvinyl pyrrolidone (PVP), acrylic acid-based polymers, polyvinyl alcohols, polyethylene glycol, cellulose derivatives such as cellulose, methyl cellulose, and hydroxypropyl cellulose; sugars such as mannan, chitosan, guar gum, xanthan gum, gum arabic, glucose, and sucrose; amino acids and the derivatives thereof such as glycine, serine, and gelatin; and natural polymers such as polylactic acid, sodium alginate, and casein. In this embodiment, PVP or an acrylic acid-based polymer can be used, in view of excellent compatibility with the underlying lead and excellent operability at the time of inserting or withdrawing the lead.

As described herein, concerns are raised by the tissue damage done when a cochlear lead is implanted. Additionally, in some patients, the presence of the implant activates the patient's immune response resulting in a rejection of the implant. To address these issues, a steroid substance applied to surgically disrupted tissues can improve patient outcomes. The advantages of locally delivered drugs include increased local and decreased systemic drug concentration thereby lessening the potential for serious side effects. Steroids, such as Dexamethasone (DEX), can help control inflammation and autoimmune responses. Dexamethasone is a potent synthetic member of the glucocorticoid class of steroid hormones. Dexamethosone demonstrates glucocorticoid (suppressing allergic, inflammatory, and autoimmune reactions) effects and serves as an antiphlogistic (anti-inflammatory) agent. Its potency is about 20-30 times that of hydrocortisone and 4-5 times that of prednisone.

When dexamethasone or its derivatives are mentioned in literature, it is invariably a reference to a dexamethasone salt. Dexamethasone salts, such as dexamethasone sodium phosphate, dexamethasone acetate, dexamethasone sulfate, dexamathasone isonicontinate, etc., are used because the water solubility of the salts forms of dexamethasone are much greater than the base form. Consequently, the salt forms were thought to be more easily delivered to living tissues and appear to be used exclusively in the prior art.

However, the inventors discovered that dexamethasone base (DXMb), which has a very low solubility in aqueous solutions, was surprisingly efficacious when administered into the intracochlear space after implantation surgeries. Additionally, DXMb was surprisingly more potent than salt forms of dexamethasone. In one study performed by the Applicants, a comparison of DXMb and DEX salt was performed in an in-vivo model over the prior of a week. The Applicants found that DXMb delivered at 1 uL/hr at a concentration of 70 uL/ml (limit of DXMb solubility in aq solution) was just as effective DEX salt delivered at a concentration of 100 uL/ml at 1 uL/hr. This surprising potency allows for increased therapeutic effects without increasing the volume of the drug or the size of the intracochlear lead.

The efficacy of DXMb was also studied by the Applicants in relationship to preserving residual hearing and internal nerve structures within the cochlea. In the study performed by the applicants, 88 ears of 44 pigmented guinea pigs of 250 to 300 grams were randomly assigned to one of four groups as follows: group 1 corresponded to the contralateral, unoperated ears from groups 2 to 4 animals (n=44). Group 2 (n=15): electrode insertion trauma (EIT); these ears underwent EIT only via a cochleostomy and then immediate closure. Group 3 (n=15): EIT+artificial perilymph (EIT+AP) treated ears received EIT and immediately after trauma, insertion of a microcatheter into the cochleostomy site with AP perfused into the scala tympani (ST) for a period of 8 days. Group 4 (n=14): EIT dexamethasone base (EIT=DXMb) treated animals underwent EIT followed immediately by insertion of a microcatheter into the cochleostomy with ST perfusion of DXMb (70 g/mL) in AP for a period of 8 days. Hearing measurements were performed before surgery, as well as on post-EIT days 0, 3, 7, 14, and 30. Tone bursts of 0.5, 1, 4, and 16 kHz were delivered to the ear at a rate of 29 Hz. The intensity of the stimulation was decreased by 10 dB sound pressure level (SPL) decrements until no auditory brainstem response was identified.

Figure 9:
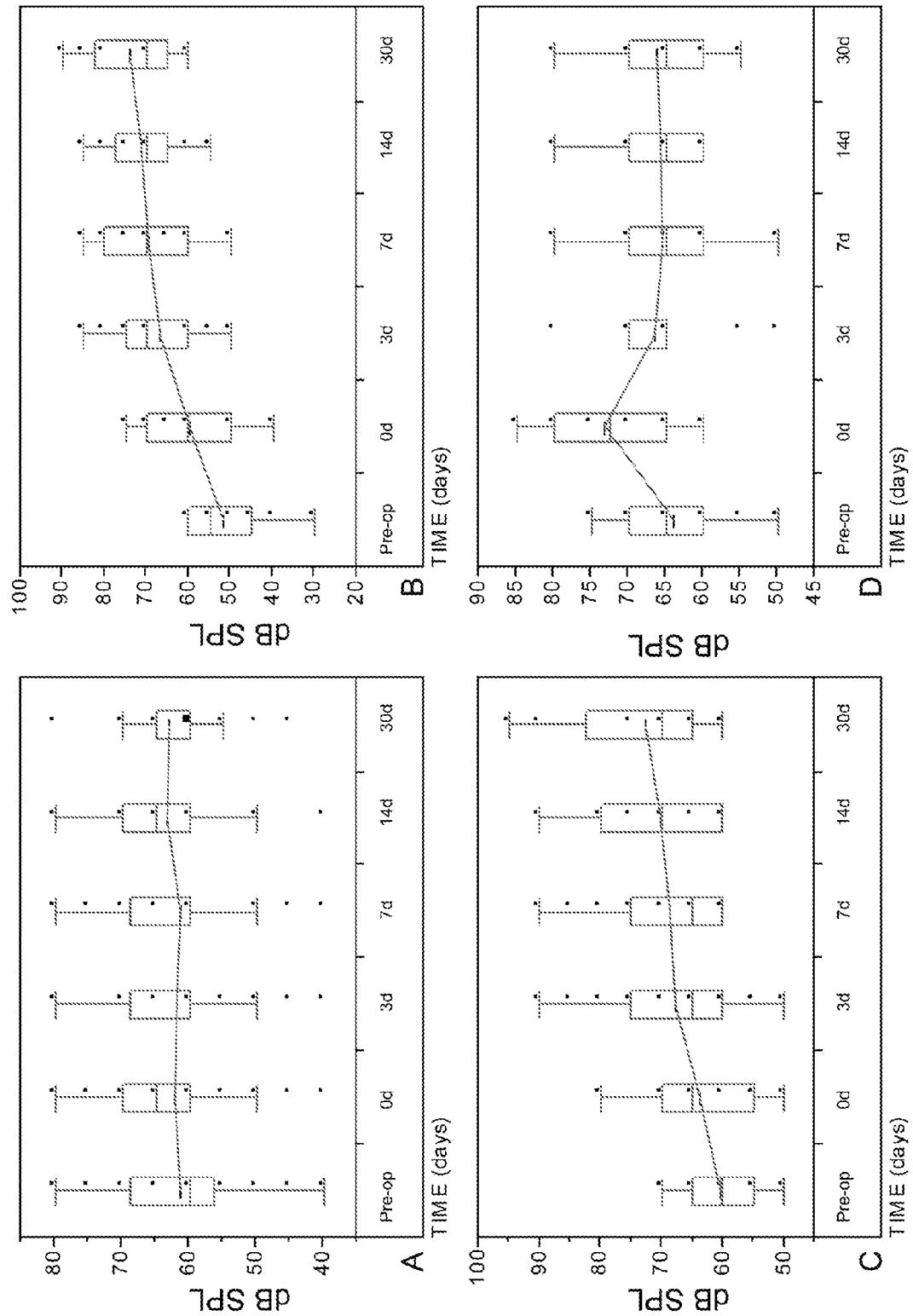
FIG. 9 is a graph which illustrates the effectiveness of dexamethasone base (DXMb) steroid in minimizing surgery induced hearing loss, according to one embodiment of principles described herein.

FIG. 9 shows charts auditory functions of the various test groups as a function of time. Each of the charts show box plots of mean auditory brainstem response threshold values by time for a set of low (0.5 kHz) frequency pure tone stimuli. A line passes through mean value of each the temporal measurement. The ends of the boxes are the 25th and 75th quartiles. The horizontal line across the middle of the boxes identifies the median threshold values. The whiskers at the ends of the boxes extend to the outermost data points. (A) Represents values for the control ears (group 1, n=44), (B) for group 2 (EIT, n=15), (C) for group 3 (EIT+AP, n=15), and (D) for group 4 (EIT+DXMb, n=14).

Chart A in FIG. 9 shows that there is no change the hearing capability in the control ears which have not been disturbed by surgery. Chart B shows that there is significant hearing loss (the measurements trend higher, showing that an increase tone volume is required to detect an auditory brainstem response) for ears where there was surgery performed but no treatment was provided. Similarly, Chart C shows that there was a significant hearing loss in ears where a placebo (artificial perilymph) was administered. Chart D shows test results for ears where DXMb was administered. In Chart D, there was a sharp increase in hearing loss immediately following the surgery, but this hearing loss was reversed by the administration of the DXMb. Over the long term, the administration of DXMb maintained the pre-operative hearing levels.

Figure 10:
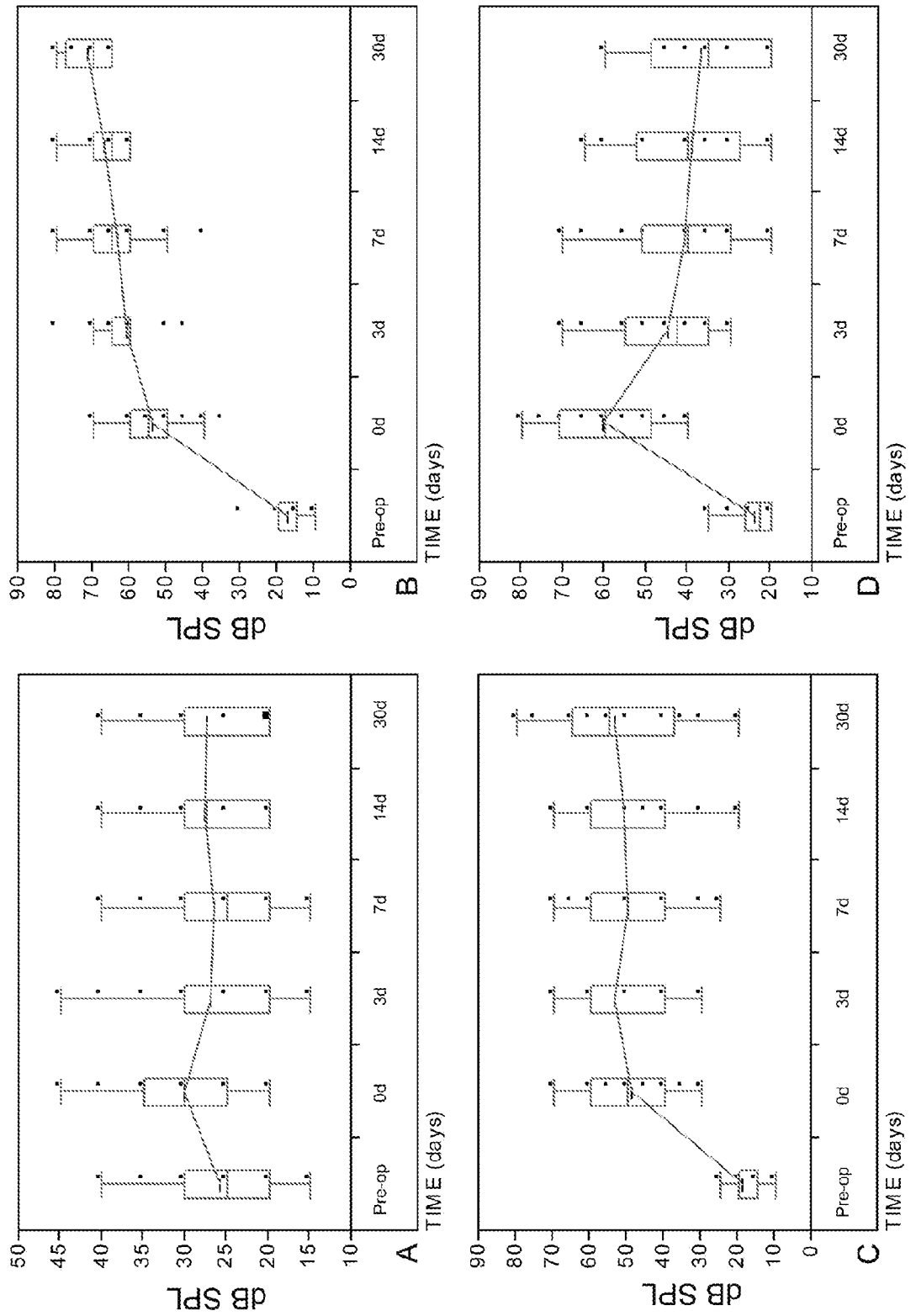
FIG. 10 is a graph which illustrates the effectiveness of DXMb steroid in minimizing surgery induced hearing loss, according to one embodiment of principles described herein.

FIG. 10 shows that DXMb treatment similarly conserves auditory function thresholds at 16 kHz after electrode insertion trauma. Chart A shows that there is no significant change the hearing capability in the control ears which have not been disturbed by surgery. Chart B shows that there is dramatic hearing loss for ears where there was surgery performed but no treatment was provided. Chart C shows that there was a less dramatic but still significant hearing loss in ears where a placebo was administered. Chart D shows test results for ears where DXMb was administered. In Chart D, there was a sharp increase in hearing loss immediately following the surgery, but this hearing loss was reversed, and continued to decline as DXMb was administrated. Consequently, it can be concluded that DXMb treatment can conserve auditory function thresholds over a range of frequencies after electrode insertion trauma.

Figure 11:
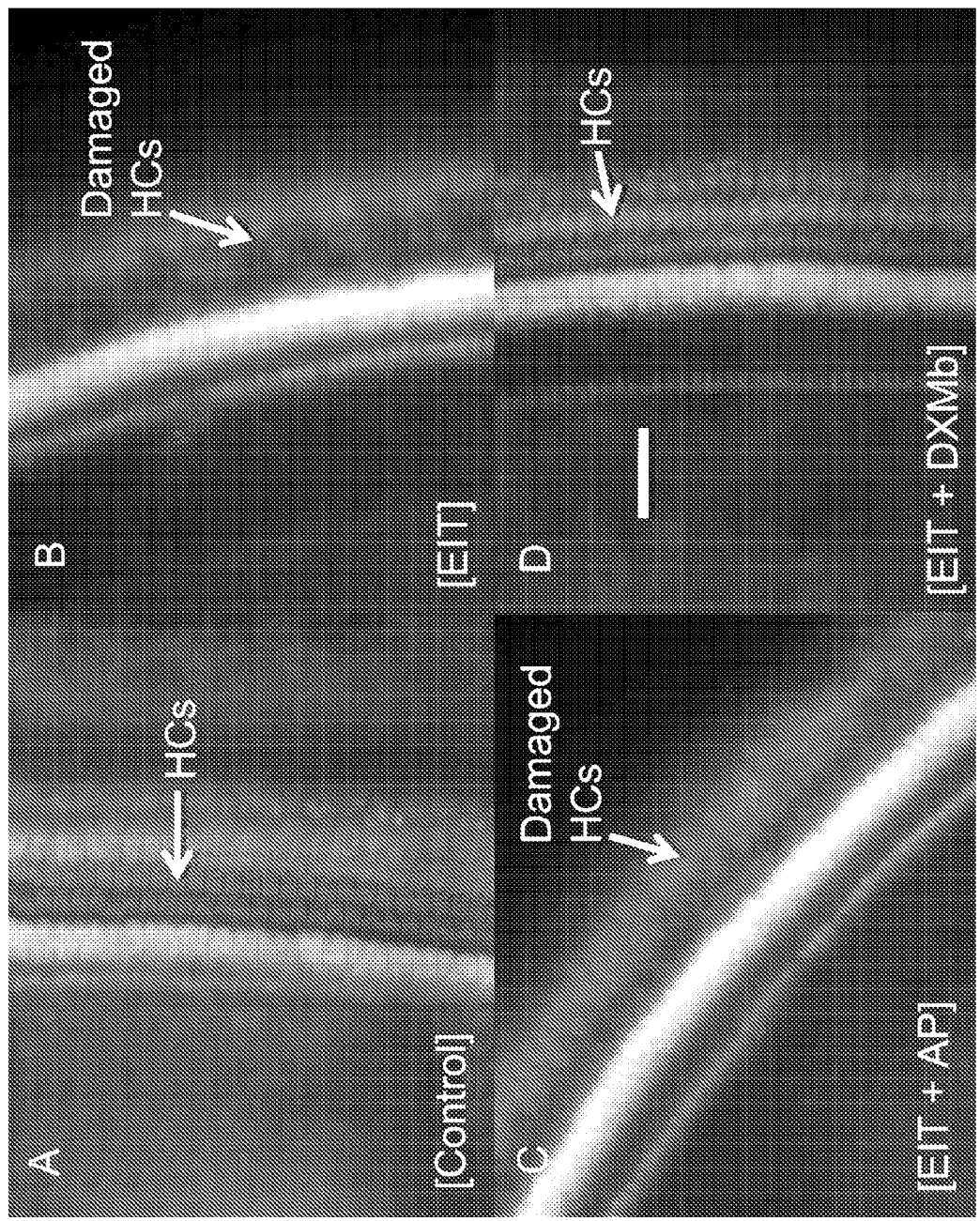
FIG. 11 shows the efficacy of DXMb protecting the auditory hair cells from electrode insertion trauma, according to one embodiment of principles described herein.

FIG. 11 shows Organ of Corti photomicrographs from an area of the lower middle turn of four representative cochleae thirty days after electrode insertion trauma. The control specimen (photomicrograph A) is the contralateral unoperated cochlea which shows the undamaged structure of hair cells (arrow, "HCs"). The organization of hair cells is in three distinct rows. Microphotograph B shows an area of damaged hair cells (arrow, "Damaged HCs") from the group which received no treatment following electrode insertion trauma. Microphotograph C shows an area of damaged hair cells (arrow, "Damaged HCs") from the group which received a placebo treatment. However, microphotograph C shows that there are fewer missing hair cells than shown in B. A possible explanation for the better preservation of hair cells receiving the placebo treatment (the cochlea was flushed with artificial perilymph rather than DXMb) was that the flushing action reduced the autoimmune actors in the intracochlear space. Microphotograph D is a photograph of hair cells from a specimen that received DXMb treatment following electrode insertion trauma. The hair cells and hair cell structure of microphotograph D are substantially similar to that of the control group, showing that DXMb treatment is effective in reducing damage to intracochlear structures following electrode insertion trauma.

As mentioned above, optimal delivery of a steroid as a means of minimizing negative surgical side effects varies by situation, but typically delivery directly to the disturbed tissues is desired. For example, the base or salt form of Dexamethasone can be combined with either or both of a surface lubricant or the underlying silicone. The sodium salt form of dexamethasone is highly soluble in aqueous preparations which allows for the application of very high dose levels of this synthetic corticosteroid if required. In contrast, the base variant of dexamethasone (i.e., DXMb) is highly soluble in organic solvents but has limited solubility in aqueous preparations. This difference in solubility between the salt and base forms of dexamethasone can be leveraged to provide a time varying release profile of steroid into the intracochlear space. For example, a high dosage of steroid is often found to beneficial during or immediately following the surgery and implantation process. This high dosage of steroid or other anti-inflammatory drug can mitigate swelling, nerve damage, and aid in the post operative recovery of the patient. For a period of time after the surgery, a lower level and sustained release of steroid or other medication can be desirable to prevent immune system rejection of the cochlear implant, ossification, tissue build up within the cochlea, and progressive nerve damage.

The combination of DEX salt and DXMb can provide a time varying release of steroids. According to one illustrative embodiment, various layers of drugs could be applied to achieve the desired release profile and combination of drugs. For example, an outer layer could be composed of DEX salt and an inner layer could be composed of DXMb. The outer layer of DEX salt would be rapidly released during the implantation, while the inner layer of DEX salt would be more slowly released for long term treatment. Other drugs could be used in combination with DEX salts or DXMb to supply a broader spectrum of benefits. By way of example and not limitation a heparin layer could be added as a thrombin inhibitor. The layering sequence and compositions could also be used to control the release rate of various drugs. For example, a heparin under layer could be used to increase the release rate of an overlying DEX salts or DXMb by about a factor of 10. The various layers could be applied using a variety of techniques. By way of example and not limitation, the layers could be applied by painting, spraying, printing (similar to ink jet technology using large or very small (picoliter) droplets), and/or dipping the lead until the desired dose is applied.

In one illustrative embodiment, the DEX salt or DXMb could be dissolved in a carrier fluid and applied to cochlear lead surface. The carrier would then evaporate or otherwise be removed, leaving the DEX salt or DXMb layer or layers in place on the cochlear lead. A number of solvents could be used. For DEX salt coatings, various aqueous solutions could be used. For DXMb coatings, organic solvents could be used. By way of example and not limitation, these organic solvents may include methanol, ethanol, isopropanol, acetone, chloroform, and others. A variety of factors could influence the choice of carrier solutions, including: the solubility of DEX salt or DXMb in the chosen solution, the evaporation rate of the carrier, the ease of applying and handling the solution, the toxicity of any remaining carrier, the compatibility of the carrier with the underlying substrates, and other factors.

Figure 12:
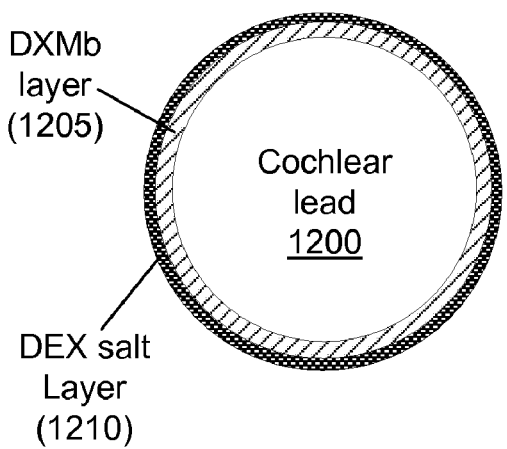
FIG. 12 a cross-sectional diagram of one illustrative cochlear lead with various coatings, according to one embodiment of principles described herein.

FIG. 12 is a cross-sectional diagram of a cochlear lead (1200) that is coated with multiple drug eluting layers (1205, 1210). According to one illustrative embodiment, a first layer (1210) containing DXMb is deposited on the outer surface of the cochlear lead (1200). A second layer (1210) containing a DEX salt is deposited over the first layer (1210). As discussed above, the DEX salt highly soluble in water or solutions that contain a high percentage of water. The intracochlear fluid is primarily water. Consequently, the DEX salt is quickly dissolved by the intracochlear fluid and rapidly attains a relatively high concentration of DEX salt within the fluid. By configuring the cochlear implant to make available a given amount of DEX salt from the second layer (1210) during and immediately after implantation, the desired burst of steroid can be administered. After the initial release of DEX salt, the DXMb contained within the second layer (1205) can provide lower levels of steroid within the cochlea for a sustained period. The saturation concentrations of DXMb within the cochlear fluid is much lower than that of DEX salt, leading to a slower release/dissolution of the DXMb into the cochlear fluid. Additionally, as described above, it has been found that DXMb can be more potent on a per mass basis than a DEX salt. This allows a larger therapeutic dose of DXMb to be delivered within the size constraints imposed by the cochlea and electrode geometries. Although no concrete explanation for the higher potency is provided, this could possibly be due to longer clearance times of DXMb. A clearance time is measurement of the time during which a drug remains within a portion of the body before it is transported or otherwise removed from the body. The lower solubility of the DXMb may lead to slower transport of the DXMb out of the intracochlear region.

Figure 13:
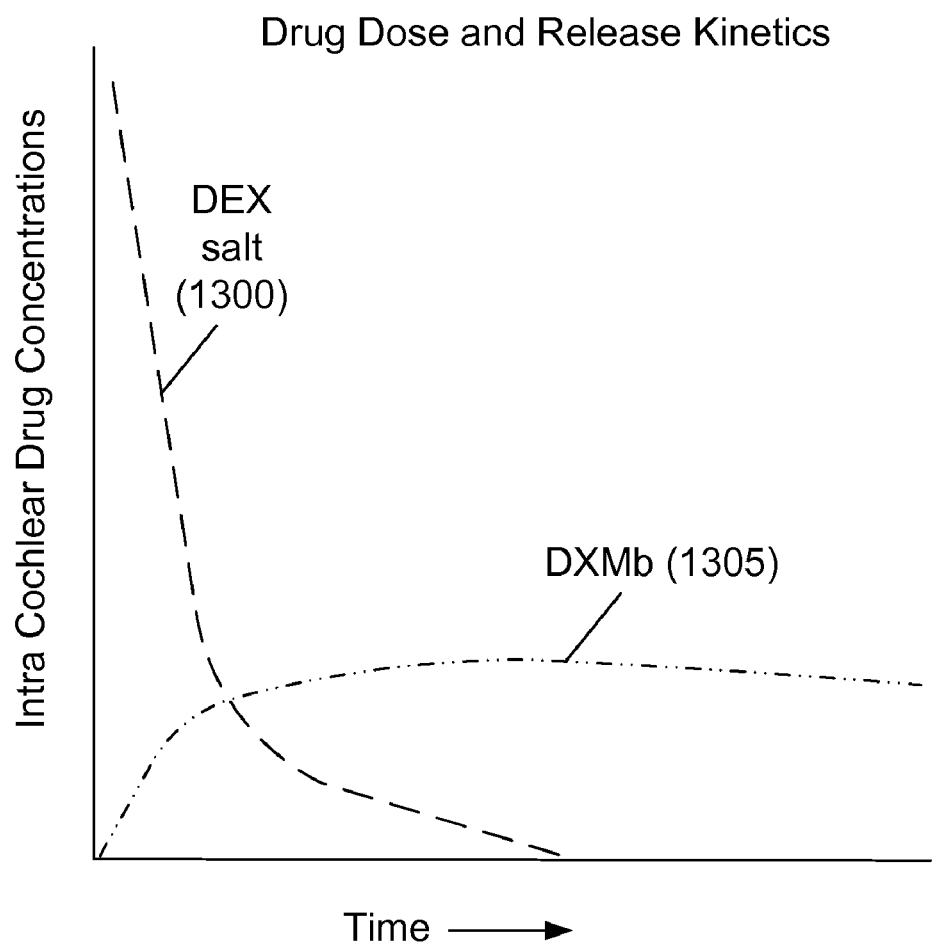
FIG. 13 an illustrative graph of drug dose and release kinematics, according to one embodiment of principles described herein.

FIG. 13 shows a chart illustrating hypothetical drug dose and release kinetics associated with a DEX salt/DXMb combination, such as the geometry illustrated in FIG. 12. The horizontal axis of the chart represents the passage of time after administration of the DEX salt/DXMb combination. The vertical axis represents the intracochlear drug concentrations. A dashed line (1300) illustrates a hypothetical release profile for DEX salt. As shown by the dashed line (1300), the DEX salt is rapidly dissolved by the intracochlear fluid and, due to the high solubility of the DEX salt in the intracochlear fluid, a high concentration of DEX salt rapidly accumulates in the cochlea. This high concentration of DEX salt mitigates the immediate damage caused by the electrode insertion. The concentration of the DEX salt rapidly declines as the DEX salt is consumed and/or transported out of the cochlea. The DXMb concentrations are illustrated by a dot-dash line (1305). The DXMb concentrations increase much more slowly and are sustained within the intracochlear space for a longer period of time.

The DEX salt/DXMb combination could be combined with the cochlear implant in a number of alternative methods. For example, a cochlear implant could be coated with a hydrophilic layer. The hydrophilic layer could be made up of a number of materials that would absorb or retain an aqueous solution, such as a "slippery when wet" lubricant or a hydrogel such as HYDROMER polyvinyl pyrrolidone. A DEX salt or a combination of DEX salt and DXMb could be dissolved in the solution. The aqueous solution could then be used to load the hydrophilic layer with DEX salt or DXMb. In one embodiment, the all or a portion of the cochlear implant could packaged and shipped in the solution. In other embodiments, the cochlear implant could be soaked in the DEX solution prior to use. In one illustrative embodiment, the solution could include a combination of aqueous and organic solvents to provide the desired delivery of DEX salt and DXMb.

Figure 14:
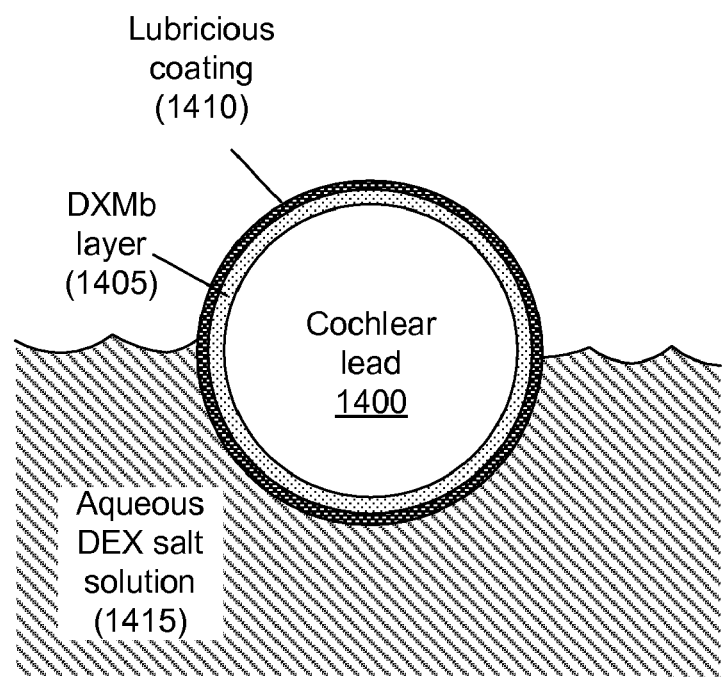
FIG. 14 a cross-sectional diagram of an illustrative cochlear lead with various coatings, according to one embodiment of principles described herein.

FIG. 14 shows an alternative embodiment of a cochlear lead (1400) where a DXMb layer (1405) is applied to the cochlear lead (1400), followed by a lubricant layer (1410). Prior to the insertion of the cochlear lead (1400) into the body tissues, the lead is submerged in an aqueous solution containing DEX salt (1415). The aqueous solution (1415) is absorbed by the lubricant layer (1410). This hydrates the lubricant and reduces the coefficient of friction between the cochlear lead (1400) and the surrounding tissues. Additionally, a portion of the DEX salt is eluted out of the lubricant layer (1410) as the cochlear lead passes through the tissues, thereby directly depositing the steroid on the disturbed tissues. Further, because the DXMb layer (1405) has only a low solubility in aqueous solutions, it will not dissolve or lose its structural integrity during the hydration and insertion process.

Another advantage of DXMb relates to its high solubility in organic solvents. Organic solvents are used in a variety of processes, including the preparation of polymers. By dissolving DXMb in an organic solvent, DXMb can be easily incorporated into a variety of biocompatible polymers. The DXMb can then be gradually eluted from the polymer to produce the desired drug release kinetics.

Figure 15:
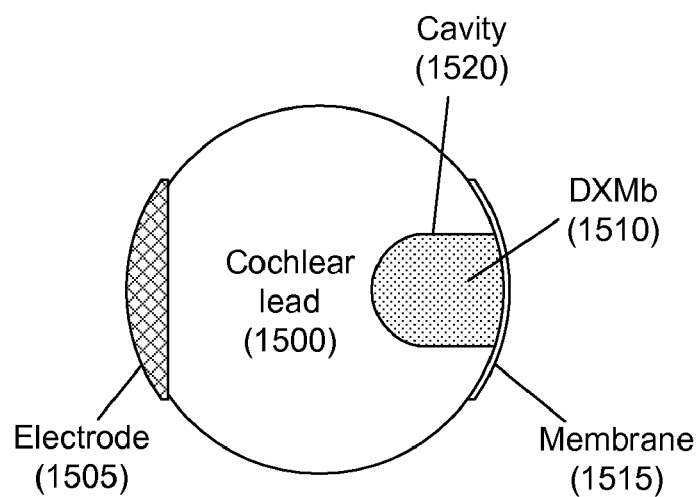
FIG. 15 a cross-sectional diagram of an illustrative cochlear lead with a cavity containing DXMb, according to one embodiment of principles described herein.

FIG. 15 shows a cross-sectional diagram of a cochlear lead (1500) with an electrode (1505) and a cavity (1520) which runs along the length of the intracochlear lead (1500). The cavity (1520) could have a variety of geometries as best suits the situation. For example, the cross-sectional shape of the cavity (1520) could be altered to best retain and dispense the drug or drug combination contained within the cavity (1520). According to one illustrative embodiment, the cavity (1520) is filled with a matrix which contains DXMb (1510). As described, above DXMb can be incorporated into a number of biocompatible polymers. This drug loaded polymer can be shaped to fill a variety of cavity geometries. According to one embodiment, the drug loaded polymer may adhere to the cavity wall or be applied as a coating to the cochlear lead surface.

In an alternative embodiment, powdered drugs or drug combinations may be used to fill the cavity (1520). A selectively permeable membrane (1515) may be used to cover the opening of the cavity (1520) and retain the powder. When the cochlear implant is inserted into tissue or the intracochlear space, body fluids pass through the membrane and dissolve the drug particles, which then pass through the membrane and into the surrounding tissues. According to one exemplary embodiment, DXMb powder (1510) is used to fill the tissue, and a membrane (1515) having a pore size of no greater than 10 microns is used to retain the DXMb powder (1510). The membrane (1515) pore size is configured to prevent the passage of bacteria across the membrane but allows water and dissolved DXMb cross the membrane. In other embodiments, the membrane may have pore sizes that range from nanofeatures to very large macroscopic holes. In one illustrative embodiment, the membrane may be eliminated entirely and the solution may directly enter the cavity.

Alternatively or additionally, the outer covering of the cochlear implant could be molded with features which facilitate the retention of DEX and any carrier medium. By way of example and not limitation the outer covering of the insulating silicone could be molded with grooves, wells, indentations, or cavities. According to one exemplary embodiment, a porous coating made from a hydrophilic polymer covers the implant lead and is configured to be impregnated with various drug eluting substances. In one illustrative embodiment, a suspension of silicone and DEX could be inserted into these features and transported into the cochlea, where the DEX could be released into the intra cochlear space. In an alternative embodiment, these features can be filled with drugs in a powered form. A thin layer or layer of variable thickness of silicone or other coating polymer could be applied to seal or partially seal the hole to give rise to the desired release kinetics. A number of factors could influence the release kinetics. By way of example and not limitation, these factors could include the permeability of the covering membrane to intracochlear or body fluids, the permeability of the covering membrane to the drug or combination of drug in the interior, the surface area of the covering membrane, the quantity of drug powder, the solubility of the drug powder, the range of particulate sizes in the powder, and other factors. As discussed above, DEX salt, DXMb, and other therapeutic drugs could be combined to deliver the desired therapeutic effect.

The various therapeutic drugs can be combined with polymers in various geometries to assist in the desired delivery. For example, in some circumstances, it may be desirable to control the elution rate of various drugs by overcoating the drug layers with a polymeric layer. According to one embodiment, the overcoating polymeric layer may be deposited by vapor or plasma deposition of the polymer agent to create a porous membrane. This allows the deposition of the overcoat without the use of solvents, catalysts, heat or other chemicals or techniques which would cause damage to the agent, drug, or material. The polymeric overcoat layer can allow for less retention of unused drug within in the implanted device. Additionally, the polymeric overcoat can prevent undesirable fragmentation of biodegradable interior substances.

In conjunction with the methods mentioned above, a variety of surface treatments can be used to render the surface more amenable to the subsequent processes. By way of example and not limitation, these methods can include cleaning physical modifications such as etching, drilling, cutting, or abrasion; and chemical modifications such as solvent treatment, the application of primer coatings, the application of surfactants, plasma treatment, ion bombardment, and covalent bonding.

By way of example and not limitation, examples of biodegradable polymers which can be used as a matrix to contain and dispense various therapeutic compounds may be selected from suitable members of the following, among many others: (a) polyester homopolymers and copolymers such as polyglycolide, poly-L-lactide, poly-D-lactide, poly-D,L-lactide, poly(beta-hydroxybutyrate), poly-D-gluconate, poly-L-gluconate, poly-D,L-gluconate, poly(epsilon caprolactone), poly(delta-valerolactone), poly(p-dioxanone), poly(trimethylene carbonate), poly(lactide-co-glycolide) (PLGA), poly (lactide-co-delta-valerolactone), poly(lactide-co-epsilon-caprolactone), poly(lactide-co-beta-malic acid), poly(lactide-co-trimethylene carbonate), poly(glycolide-co-trimethylene carbonate), poly(beta-hydroxybutyrate-co-beta-hydroxyvalerate), poly[1,3-bis(p-carboxyphenoxy)propane-co-sebacic acid], and poly(sebacic acid-co-fumaric acid), among others, (b) poly(ortho esters) such as those synthesized by copolymerization of various diketene acetals and diols, among others, (c) polyanhydrides such as poly(adipic anhydride), poly (suberic anhydride), poly(sebacic anhydride), poly (dodecaned oic anhydride), poly(maleic anhydride), poly[1, 3-bis(p-carboxyphenoxy)methane anhydride], and poly [alpha,omega-bis(p-carboxyphenoxy)alkane anhydrides] such aspoly[1,3-bis(p-carboxyphenoxy)propane anhydride] and poly[1,3-bis(p-carboxyphenoxy)hexane anhydride], among others; and (d) amino-acid-based polymers including tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and tyrosine-, leucine- and lysine-based polyester-amides; specific examples of tyrosine-based polymers include includes polymers that are comprised of a combination of desaminotyrosyl tyrosine hexyl ester, desaminotyrosyl tyrosine, and various di-acids, for example, succinic acid and adipic acid, among others.

According to one embodiment, DXMb may also be delivered in bio-release polymer matrix. The bio-release polymer matrix containing DXMb may be used and shaped in a variety of ways. By way of example and not limitation, a cochlear implant electrode array coated with a DXMb impregnated polymer that can bio-release this drug at a predetermined rate that is determined at the time of fabrication.

According to one exemplary embodiment, the various drug components can be incorporated into a polymeric matrix, which is then applied to the cochlear lead. The polymeric matrix layer may be fabricated in a variety of ways. By way of example and not limitation, a mixture can be formed from 0.2 milligrams of dexamethasone sodium phosphate with 0.5 cubic centimeters of silicone medical adhesive. The mixture is molded to the desired shape and allowed to cure. After curing the polymeric matrix layer is attached to the outer substrate with silicone medical adhesive such as SILASTIC by Dow Corning. The thickness of the drug impregnated polymeric coating can be varied to deliver the optimal amount of drug dosage over the lifetime of the device. The coating may also cover varying portions of the implant. For example, the coating may cover the entire implant lead or may be applied to only a portion of the lead so that the electrodes are not covered.

Polymer matrix which as been impregnated with DXMb or another drug can be shaped into a variety of geometries and incorporated into a cavity within the lead. This cavity may be covered by a porous elution path. The porous elution path may be created by placing a layer of cindered platinum or titanium foam over the cavity opening. According to one embodiment, the particles of DEX salts or DXMb, combinations there of, can be mixed with silicone rubber medical adhesive. The silicon rubber medical adhesive is permeable by water vapor, which dissolves the DEX salts or DXMb. The dissolved DEX salts or DXMb then elute from the matrix into the cochlear space. In one illustrative embodiment, particles of dexamethasone sodium phosphate, which has a relatively fast elution rate, and particles of DXMb, which has a much slower elution rate, can be use in combination to achieve the desired release profile. As mentioned above, a number of other factors, such as particle size, surface area, matrix, etc. can be used to further adjust the drug release over time.

In an alternative embodiment, a silicone elastomer matrix is used rather than silicon medical adhesive. The silicon elastomer may provide a number of manufacturing advantages including longer pot life and a shorter curing time. According to one illustrative method, two silicon elastomer precursor compounds are combined with a third compound which carries the drug particles. The third compound may be silicone fluid and the drug particles may be made up of DXMb or similar compound. The three components are mixed and placed in a mold. The temperature of the matrix and mold can be controlled to assist in curing the matrix. After the molding process is complete, the silicon shape can be placed in or on the cochlear lead as desired.

All of the above methods of dispensing therapeutic compounds can be combined with various lubrication techniques. Additionally, the drug layer may have lubricant properties or a lubrication layer which contains drug compounds may be included.

Figure 16:
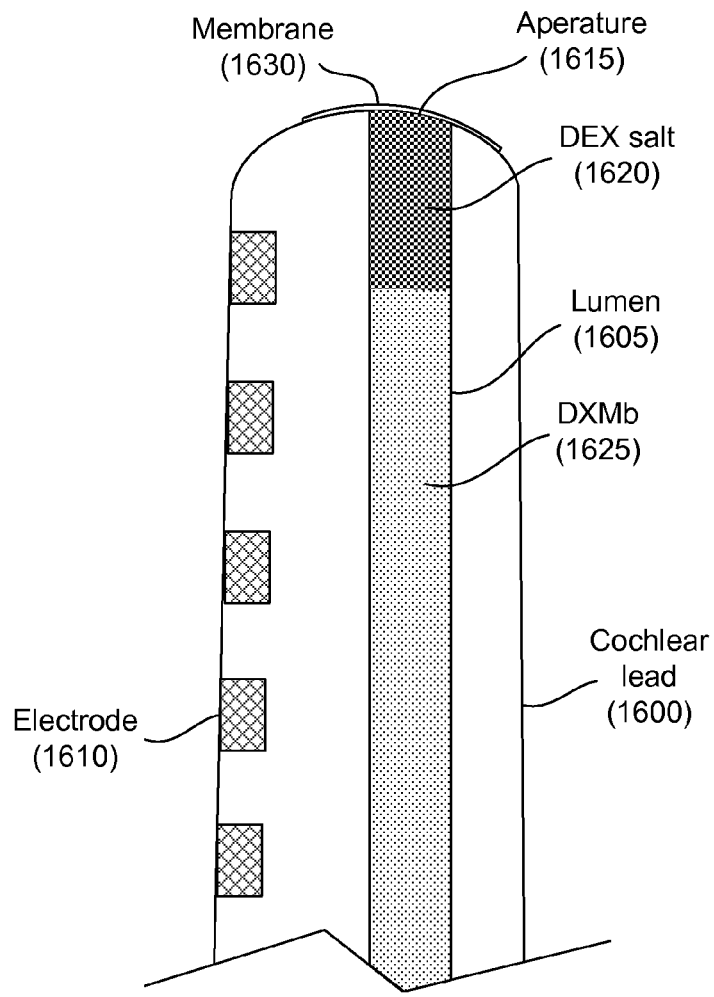
FIG. 16 a longitudinal section of an illustrative cochlear lead with a longitudinal lumen configured to accept various drug compounds, according to one embodiment of principles described herein.
Figure 17:
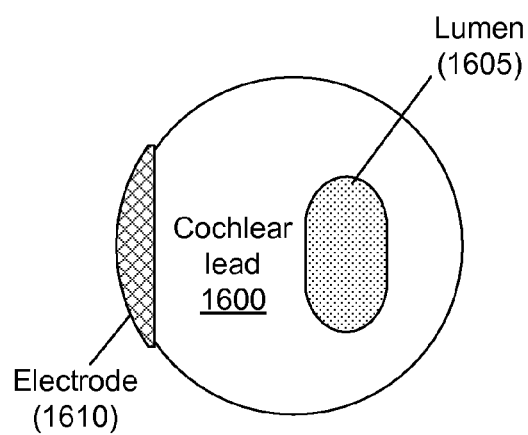
FIG. 17 a cross-sectional diagram of illustrative cochlear lead with a longitudinal lumen configured to accept various drug compounds, according to one embodiment of principles described herein.

FIGS. 16 and 17 show an illustrative embodiment of a cochlear lead (1600) with various electrodes (1610) along one side and a lumen (1605) passing longitudinally through the cochlear lead. The lumen (1605) may access the surrounding tissues through one or more apertures (1615). According to one embodiment, the lumen (1605) may serve as a drug reservoir. For example, the lumen (1605) could contain a powdered DEX salt (1620) near the aperture (1615) and powdered DXMb (1625) in the remainder of the lumen (1605). The aperture (1615) could be covered with a membrane (1630) to retain the drug powders (1620, 1625) and control the passage of solutes and particles through the aperture (1615). Additionally or alternatively, the lumen (1605) could be filled with a suspension of silicone and DEX salt/DXMb. The lumen could be filled with the drug or drug eluting compound during manufacturing or just prior to use.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A method for delivering dexamethasone base (DXMb) via an implantable electrode comprising:
    coupling said DXMb and dexamethasone (DEX) salt to said implantable electrode by:
        coating said implantable electrode with a layer of DXMb,
        overcoating said layer of DXMb with a hydrophilic lubricant, and
        applying a solution containing said DEX salt to said lubricant by soaking said implantable electrode in a solution containing DEX salt prior to use said solution being absorbed by said lubricant; and
    inserting said implantable electrode into biological tissue, said DXMb and said DEX salt eluting into said biological tissue, wherein said DEX salt is configured to rapidly elute into said biological tissue and said DXMb is configured to more slowly elute into said biological tissue at a lower concentration than said DEX salt.

2. The method of claim 1, wherein, said implantable electrode is configured to be inserted into a cochlea.

3. The method of claim 1, wherein said lubricant comprises a slippery when wet lubricant.

4. A method for delivering dexamethasone base (DXMb) via an implantable electrode comprising:
    coupling said DXMb to said implantable electrode by coating said implantable electrode with a layer of DXMb;
    overcoating said layer of DXMb with a hydrophilic lubrication layer;
    applying a solution containing dexamethasone (DEX) salt to said lubrication layer, said solution being absorbed by said lubrication layer; and
    inserting said implantable electrode into biological tissue, said DXMb eluting into said biological tissue.

5. The method of claim 4, wherein said lubrication layer comprises a slippery when wet lubricant.

6. An implantable nerve stimulating device comprising:
    an elongated member having a distal end bearing at least one electrode; and DXMb coupled to said elongated member;
DEX salt deposited over said DXMb;
wherein said DEX salt is configured to rapidly elute into surrounding tissue when the device is implanted and said DXMb is configured to more slowly elute into said surrounding tissue at a lower concentration than the DEX salt.

* * * * *